(12) United States Patent
Rosenbluth et al.

(10) Patent No.: US 9,576,108 B2
(45) Date of Patent: Feb. 21, 2017

(54) METHOD FOR DETERMINING AN INFUSION PARAMETER

(75) Inventors: Kathryn H. Rosenbluth, San Francisco, CA (US); Jan Felix Eschermann, Munich (DE); Joseph Doyle, Munich (DE); Krystof Bankiewicz, Oakland, CA (US); Stephan Mittermeyer, Munich (DE)

(73) Assignee: Brainlab AG, Munich (DE)

( * ) Notice: Subject to any disclaimer, the term of this patent is extended or adjusted under 35 U.S.C. 154(b) by 56 days.

(21) Appl. No.: 14/371,758

(22) PCT Filed: Feb. 2, 2012

(86) PCT No.: PCT/EP2012/051751
§ 371 (c)(1),
(2), (4) Date: Jul. 11, 2014

(87) PCT Pub. No.: WO2013/113391
PCT Pub. Date: Aug. 8, 2013

(65) Prior Publication Data
US 2014/0358114 A1  Dec. 4, 2014

(51) Int. Cl.
*G06K 9/00* (2006.01)
*G06F 19/00* (2011.01)

(52) U.S. Cl.
CPC .................. *G06F 19/3468* (2013.01)

(58) Field of Classification Search
None
See application file for complete search history.

(56) References Cited

U.S. PATENT DOCUMENTS

| | | | |
|---|---|---|---|
| 7,266,227 B2 * | 9/2007 | Pedain | A61B 19/52 382/128 |
| 7,715,902 B2 * | 5/2010 | Hartlep | A61B 5/055 382/128 |

(Continued)

OTHER PUBLICATIONS

Machado, Andre, et al. "Deep brain stimulation for Parkinson's disease: surgical technique and perioperative management." Movement disorders21.S14 (2006): S247-S258.*

(Continued)

*Primary Examiner* — Vu Le
*Assistant Examiner* — Samah Beg
(74) *Attorney, Agent, or Firm* — Tucker Ellis LLP

(57) ABSTRACT

A method for planning an infusion of a medical substance into a target region acquires non-patient-specific anatomical data from an atlas in the form of target region geometry information describing target and off-target regions for which an infusion of the medical substance is intended and regions to be avoided, respectively. Target coverage information is derived describing a minimum dose of the medical substance to be infused into the target region and describing a maximum dose of the medical substance to be applied to the off-target region. Relationship information describes a relationship between a physical parameter of an infusion setup and a selected spatial distribution of the medical substance. Infusion setup information for the infusion is determined that describes a planned infusion setup and is based on the relationship information and information related to the target and off-target regions.

13 Claims, 13 Drawing Sheets

(56) References Cited

U.S. PATENT DOCUMENTS

| | | | | |
|---|---|---|---|---|
| 8,060,181 B2* | 11/2011 | Rodriguez Ponce | A61B 19/201 | 600/411 |
| 8,105,307 B2* | 1/2012 | Ponce | A61M 5/172 | 600/300 |
| 8,702,580 B2* | 4/2014 | Hartlep | G06F 19/3437 | 600/4 |
| 8,836,697 B2* | 9/2014 | Nord | A61N 5/1031 | 345/419 |
| 2003/0114751 A1* | 6/2003 | Pedain | A61M 5/14 | 600/431 |
| 2007/0078338 A1* | 4/2007 | Pedain | A61M 5/14 | 600/431 |
| 2007/0244387 A1* | 10/2007 | Rodriguez Ponce | G06F 19/321 | 600/411 |
| 2008/0015432 A1* | 1/2008 | Hartlep | A61M 5/14 | 600/419 |
| 2008/0131376 A1* | 6/2008 | Miura | A61K 41/0019 | 424/9.3 |
| 2008/0200804 A1* | 8/2008 | Hartlep | A61M 5/14 | 600/431 |
| 2008/0208113 A1* | 8/2008 | Damiano | A61M 5/1723 | 604/67 |
| 2010/0020931 A1* | 1/2010 | Otto | A61B 6/5241 | 378/65 |
| 2010/0092517 A1* | 4/2010 | Koman | A61K 38/4893 | 424/239.1 |
| 2010/0185133 A1* | 7/2010 | Von Busch | G06F 19/3437 | 604/5.01 |
| 2012/0123184 A1* | 5/2012 | Otto | A61N 5/1067 | 600/1 |
| 2012/0209110 A1* | 8/2012 | Bankiewicz | A61B 19/201 | 600/431 |
| 2012/0330084 A1* | 12/2012 | Pantell | A61N 5/10 | 600/1 |
| 2013/0048883 A1* | 2/2013 | Simon | A61N 5/1048 | 250/492.3 |
| 2013/0211247 A1* | 8/2013 | Kalafut | A61B 6/507 | 600/432 |
| 2013/0253415 A1* | 9/2013 | Sano | A61B 18/14 | 604/20 |
| 2013/0322714 A1* | 12/2013 | Mittermeyer | A61B 19/50 | 382/128 |
| 2014/0058747 A1* | 2/2014 | Thomson | G06F 19/345 | 705/2 |
| 2015/0018596 A1* | 1/2015 | Schulz | A61N 5/1067 | 600/1 |
| 2015/0165234 A1* | 6/2015 | Bharat | A61N 5/1064 | 600/427 |
| 2015/0174428 A1* | 6/2015 | Bzdusek | G06T 7/003 | 382/131 |
| 2015/0178467 A1* | 6/2015 | Britzen | G06F 19/3437 | 703/11 |
| 2015/0302166 A1* | 10/2015 | Thomson | G06F 17/10 | 703/2 |
| 2015/0359603 A1* | 12/2015 | Levy | A61B 34/10 | 703/2 |
| 2016/0030606 A1* | 2/2016 | Devoogdt | A61K 51/1045 | 424/1.53 |
| 2016/0059040 A1* | 3/2016 | Paliwal | A61N 5/1042 | 378/65 |
| 2016/0114192 A1* | 4/2016 | Lachaine | A61N 5/1037 | 600/1 |
| 2016/0175052 A1* | 6/2016 | Kumar | A61N 5/1037 | 600/407 |
| 2016/0237163 A1* | 8/2016 | Sariel | C07K 16/30 | |

OTHER PUBLICATIONS

Andrew et al., "Factors Affecting Drug Distribution Through Infusion" http://www.pdonlineresearch.org, Aug. 2011, pp. 1-5.

* cited by examiner

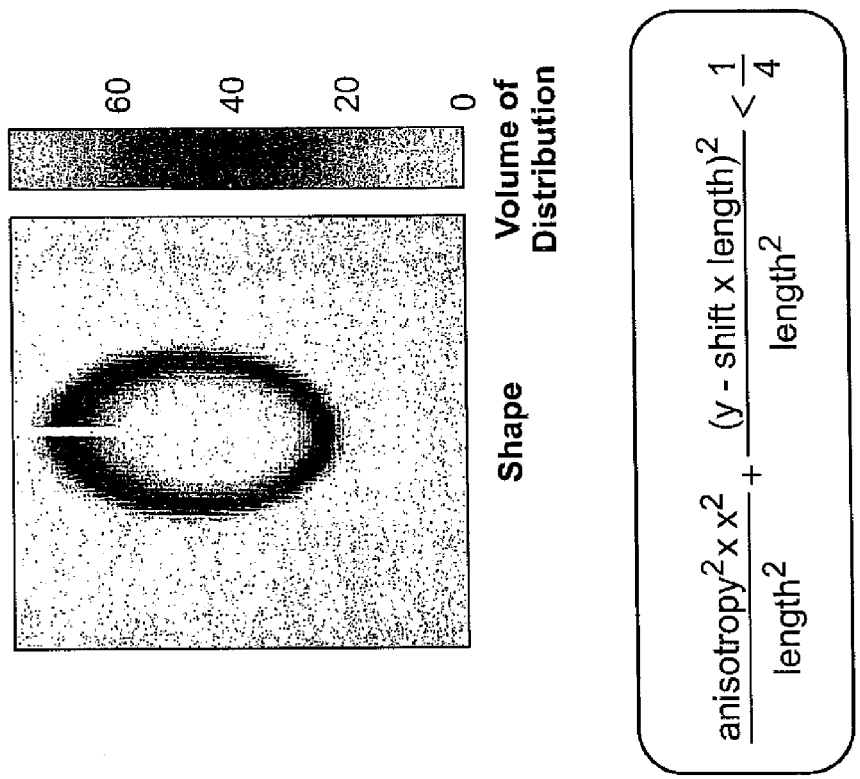

ASSUMPTIONS FOR SHAPE

- Distribution is shaped as a longitudinal spheroid oriented along the main axis of the cannula:

$$\frac{x^2}{width^2} + \frac{(y-center)^2}{length^2} < \frac{1}{4}$$

- Distribution volume scales linearly with infusion volume:

$Vd = 2.5 \times Vi$ where $Vd = 1/6\ p\ length\ width^2$

- Constant aspect ratio anisotropy = length / width = 1.5

- Constant tip location shift = tip / length = 0.16

Fig. 10b

METHOD FOR DETERMINING AN INFUSION PARAMETER

RELATED APPLICATION DATA

This application is a national phase application of International Application No. PCT/EP2012/051751 filed Feb. 2, 2012 and published in the English language.

The present invention is directed to a method for planning a medical treatment, in particular an infusion of a medical substance into a target region in an anatomical body part according to claim 1 and a corresponding program and computer running the program.

In order to optimise patient treatment by means of therapeutic agents such as pharmaceuticals, a high concentration of drug within a target region is generally desired. At the same time, exposure of surrounding healthy tissue or adjacent critical structures should be minimized, in particular to minimize toxic effects. Local drug delivery methods such as convection-enhanced delivery (CED) allow for such high local concentration profiles. However, due to complex and irregular shapes of clinical targets, planning of such treatment can be complicated. Algorithms for patient-specific, predictive modelling of the shape of the distribution of the therapeutic agent in and around the target region are available, but rely on imaging quality. In addition, computation time required for such planning renders treatment planning, in particular infusion planning, difficult.

A problem to be solved by the present invention thus is to provide a method of treatment planning, in particular infusion planning, which is simpler and more efficient than known methods.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention as long as technically sensible and feasible. In particular, a feature of one embodiment which has the same or similar function of another feature of another embodiment can be exchanged. In particular, a feature of one embodiment which supplements a further function to another embodiment can be added to the other embodiment.

The method in accordance with the invention is in particular a data processing method. The data processing method is preferably performed using technical means, in particular a computer. In particular, the data processing method is executed by or on the computer. The computer in particular comprises a processor and a memory in order to process the data, in particular electronically and/or optically. The calculating steps described are in particular performed by a computer. Determining or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term of computer encompasses a cloud computer, in particular a cloud server. The term of cloud computer encompasses cloud computer system in particular comprises a system of at least one cloud computer, in particular plural operatively interconnected cloud computers such as a server farm. Preferably, the cloud computer is connected to a wide area network such as the world wide web (WWW). Such a cloud computer is located in a so-called cloud of computers which are all connected to the world wide web. Such an infrastructure is used for cloud computing which describes computation, software, data access and storage services that do not require end-user knowledge of physical location and configuration of the computer that delivers a specific service. In particular, the term "cloud" is used as a metaphor for the internet (world wide web). In particular, the cloud provides computing infrastructure as a service (IaaS). The cloud computer may function as a virtual host for an operating system and/or data processing application which is used for executing the inventive method. Preferably, the cloud computer is an elastic compute cloud (EC2) provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals represent in particular the data received or outputted by the computer. Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit—CPU) which executes the computer program elements and optionally a volatile memory (in particular, a random access memory—RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. Preferably, the data storage medium is a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

Image data and image information comprised in any kind of image data within the framework of this disclosure is, as far as no deviating description is given, generated by imaging methods, in particular medical imaging methods. In the field of medicine, imaging methods are used to generate image data (for example, two-dimensional or three-dimensional image data) of anatomical structures (such as soft tissues, bones, organs, etc.) of the human body. Medical imaging methods are understood to mean advantageously apparatus-based imaging methods (so-called medical imaging modalities and/or radiological imaging methods), such as for instance computed tomography (CT) and cone beam computed tomography (CBCT; in particular volumetric CBCT), x-ray tomography, magnetic resonance tomography (MRT or MRI), conventional x-ray, sonography and/or ultrasound examinations, and positron emission tomography. Analytical devices are in particular used to generate the image data (in particular, analytical image data) in apparatus-based imaging methods. Analytical devices are in particular devices for analysing a patient's body, for instance by using waves and/or radiation and/or energy beams, in particular electromagnetic waves and/or radiation, ultrasound waves and/or particles beams. Analytical devices are in particular devices which generate images (for example, two-dimensional or three-dimensional images) of the patient's body (in particular, internal structures and/or anatomical parts of the patient's body) by analysing the body. Analytical devices are in particular used in medical diagnosis, in particular in radiology. However, it can be difficult to identify a treatment body part within the analytical image. Within the framework of this disclosure, a treatment body part is an anatomical body part of a patient's body to which the disclosed method of treatment or treatment planning (more specifically, infusion planning) is to be applied. In particular, a treatment body part consists of or comprises a target region. It can in particular be easier to identify an indicator body part which correlates with changes in the position of the treatment body part and in particular the movement of the treatment body part. Thus, tracking an indicator body part allows a movement of the treatment body part to be tracked on the basis of a known correlation between the changes in the position (in particular the movements) of the indicator body part and the treatment body part.

The imaging methods are in particular used for medical diagnostics, to analyse the anatomical body in order to generate images which are described by the image data. The imaging methods are in particular used to image healthy tissue or to detect pathological changes or anatomical anomalies in the human body. However, some of the changes in the anatomical structure, in particular the pathological changes in the structures (tissue), may not be detectable and in particular may not be visible in the images generated by the imaging methods. A tumour for example represents an example of a change in an anatomical structure. If the tumour grows, it may then be said to represent an expanded anatomical structure. This expanded anatomical structure may not be detectable; in particular, only a part of the expanded anatomical structure may be detectable. Primary/high-grade brain tumours are for example usually visible on MRI scans when contrast agents are used to infiltrate the tumour. The MRI scans represent an example of an imaging method. In the case of MRI scans of such brain tumours, the signal enhancement in the MRI images (due to the contrast agents infiltrating the tumour) is considered to represent the solid tumour mass. The solid tumour mass in particular constitutes or is comprised in a target region. Thus, the tumour is detectable and in particular discernable in the image generated by the imaging method. In addition to these tumours, referred to as "enhancing" tumours, it is thought that approximately 10% of brain tumours are not discernable on a scan and are in particular not visible to a user looking at the images generated by the imaging method.

Elastic fusion transformations (e.g. image fusion transformation) are in particular designed to enable a seamless transition from one data set (e.g. first data set, e.g. first image) to another data set (e.g. second data set, e.g. second image). The transformation is in particular designed such that one of the first and second data sets (images) is deformed, in particular in such a way that corresponding structures (in particular, corresponding image elements) are arranged at the same position as in the other of the first and second images. The deformed (transformed) image which is transformed from one of the first and second images is in particular as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are in particular vectors of a deformation field F. These vectors are determined by the optimisation algorithm which results in an optimum degree of similarity. Thus, the optimum degree of similarity represents a condition, in particular a constraint, for the optimisation algorithm. The bases of the vectors lie in particular at voxel positions of one of the first and second images which is to be transformed, and the tips of the vectors lie at the corresponding voxel positions in the transformed image. A plurality of these vectors are preferably provided, for instance more than twenty or a hundred or a thousand or ten thousand, etc. Preferably, there are (other) constraints on the transformation (deformation), in particular in order to avoid pathological deformations (for instance, all the voxels being shifted to the same position by the transformation). The constraints include in particular the constraint that the transformation is regular, which in particular means that a Jacobian determinant calculated from a matrix of the deformation field (in particular, the vector field) is larger than zero. The constraints include in particular the constraint that the transformed (deformed) image is not self-intersecting and in particular that the transformed (deformed) image does not comprise faults and/or ruptures. The constraints include in particular the constraint that if a regular grid is transformed simultaneously with the image and in a corresponding manner, the grid is not allowed to interfold at any of its locations. The optimising problem is in particular solved iteratively, in particular by means of an optimisation algorithm which is in particular a first-order optimisation algorithm, in particular a gradient descent algorithm. Other examples of optimisation algorithms include optimisation algorithms which do not use derivations such as the downhill simplex algorithm or algorithms which use higher-order derivatives such as Newton-like algorithms. The optimisation algorithm preferably performs a local optimisation. If there are a plurality of local optima, global algorithms such as simulated annealing or genetic algorithms can be used. In the case of linear optimisation problems, the simplex method can for instance be used.

In the steps of the optimisation algorithms, the voxels are in particular shifted by a magnitude in a direction such that the degree of similarity is increased. This magnitude is preferably less than a predefined limit, for instance less than $\frac{1}{10}$ or $\frac{1}{100}$ or $\frac{1}{1000}$ of the diameter of the image, and in particular about equal to or less than the distance between neighbouring voxels. Due in particular to a high number of (iteration) steps, large deformations can be implemented.

The determined elastic fusion transformation can be in particular used to determine a degree of similarity (similarity measure also referred to as "measure of similarity") between the first and second data set (first and second image). To this end, the deviation of the elastic fusion transformation and an identity transformation is determined. The degree of deviations can be for instance calculated by determining the difference between the determinant of the elastic fusion transformation and the identity transformation. The higher the deviation is the less is the similarity. Thus, the degree of deviation can be used to determine a measure of similarity. A measure of similarity can in particular be determined on the basis of a determined correlation between the first and second data set.

In this application, the term "image morphing" is also used as an alternative to the term "image fusion", but with the same meaning.

The present invention is also directed to a navigation system for computer-assisted surgery. This navigation system preferably comprises the aforementioned computer for processing the data provided in accordance with the data processing method as described in any one of the preceding embodiments. The navigation system preferably comprises a detection device for detecting the position of detection points which represent the position of specific devices or other physical entities such as body parts, in order to generate detection signals and to supply the generated detection signals to the computer such that the computer can determine the position of the specific devices on the basis of the detection signals received. In this way, position data comprising information about the position can be provided to the computer. The position of the specific devices or in particular body parts are preferably determined by use of marker devices such as retroreflective markers which reflect electromagnetic waves and use a corresponding detection device such as a camera. Alternatively or additionally, the positions may be determined from image data, in particular medical image data, by known methods of image analysis. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a monitor or a loudspeaker. The user interface can use any kind of indication signal (for example a visual signal, an audio signal and/or a vibration signal).

Within this disclosure, the expression "acquiring data" encompasses in particular (within the framework of a data processing method) the scenario in which the data are determined by the data processing method or program. Determining data in particular encompasses measuring physical quantities and transforming the measured values into in particular digital data and/or computing the data by means of a computer, in particular computing the data within the method of the invention. The meaning of "acquiring data" in particular also encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. The acquiring step in particular does not involve an invasive step which would represent a substantial physical interference with the body requiring professional medical expertise to be carried out and entailing a substantial health risk even when carried out with the required professional care and expertise. Acquiring, in particular determining, data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe.

Preferably, the inventive method is at least partly executed by a computer. That is, all steps or just some of the steps (i.e. less than a total number of steps) of the inventive method may be executed by a computer.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

The invention is in particular directed to a data processing method for planning a medical treatment, in particular for planning an infusion of a medical substance into a target region in an anatomical body part. In particular, the target region is located in an anatomical body part. The term of infusion encompasses any kind of procedure or technique which involves or leads to introduction of the medical substance into the target region. Within the framework of this disclosure, an anatomical body part in particular denotes a part (i.e. an anatomical structure or a body fluid) of a real patient's body which either exists in reality or is part of a virtual model of a patient's body (also called virtual patient's body). The anatomical body part in particular is for example at least part of the brain or a vessel such as a coronary artery or a bone or cartilage structure. The term of patient or (patient's) body within this disclosure encompasses both a real patient (a real patient's body) and a virtual (in particular simulated) patient (virtual patient's body). The term of medical substance encompasses any kind of substance which may be used in a medical procedure, in particular a substance used in a procedure which aims at healing a pathological condition, more particularly any substance having a healing effect such as for example a pharmaceutical. Consequently, the term of medical substance also encompasses contrast agents or isotonic fluids such as saline. The medical substance may be in any kind of state of aggregation, preferably, however, it is in a fluid or gaseous state for the purpose of the infusion to be planned.

Within the framework of this disclosure, a target region is understood to be a part of a real or virtual patient's body in which the planned medical treatment is meant to have a treatment effect. In particular, the target region is a part of the body to which the medical substance shall be applied, in particular in which it shall be physically distributed, in particular based on the principles of diffusion or pressure-driven substance distribution, more particularly pressure-driven fluid substance and/or drug distribution. A treatment effect comprises an effect which supports healing of a pathologic condition which is present in the patient's body, in particular in a treatment body part, more particularly in the target region. The treatment effect may alternatively or additionally support prevention of such a pathological condition. For the present disclosure, this in particular means that the medical substance infused into the target region is meant to have a treatment effect on the target region.

Other parts of the real or virtual patient's body are in the framework of this invention denoted as healthy tissue or critical structures. Healthy tissue and critical structures are in particular located outside the target region and are both encompassed by the term of off-target region. Healthy tissue is understood to denote an anatomical structure of the patient's body to which an application of the method according to the invention is or appears to be unavoidable if the desired treatment effect in the target region shall be achieved. However, it is desirable to avoid a detrimental effect of the planned treatment on healthy tissue as much as possible, i.e. to minimize such an effect. For example, the medical substance may influence healthy tissue in an undesirable manner, in particular by achieving toxic effects in healthy tissue. These effects shall be kept at a minimum while achieving a desired or acceptable treatment effect in the target region. The term of critical region in particular describes healthy tissue on which an influence of the planned treatment has to be avoided in any case and not only minimized as for healthy tissue in general. Examples of critical structures are vital organs such as the heart or functional regions of the brain which shall not be influenced by the medical substance in order to avoid possibly permanent detrimental effects on the patient's health and quality of life. The inventive method seeks to in particular optimise the ratio of desired effects of a medical treatment on the target region to undesired effects on off-target regions, in particular in healthy tissue and critical structures.

The medical substance is preferably infused by means of an infusion setup. The infusion setup in particular comprises an infusion device for performing the infusion as well as the medical substance itself, in particular while being placed in the infusion device ready for or during infusion. The infusion device preferably is a tubular system for leading a fluid (i.e. a liquid or gas), in particular a catheter or a cannula. The term of infusion in the context of this disclosure also encompasses the term of injection.

Preferably, relationship data comprising relationship information is acquired. The relationship information in particular describes, in particular is and/or constitutes a relationship between at least one physical parameter of the infusion setup and a predetermined spatial distribution of the medical substance intended to be achieved in the anatomical body part, in particular in the target region. In particular, the relationship information is the relationship itself. That means the relationship information in particular consists of the relationship rather than just describing it in the way metainformation would do. Where in this disclosure reference is made to a or one physical parameter, that disclosure is applicable to the at least one parameter as defined above. The physical parameter of the infusion setup according to one preferred embodiment is a physical parameter of the infusion device. In this case, the physical parameter in particular describes a geometric or surface property of the infusion device. The geometric property of the infusion device is in particular at least one of the tip length, the diameter (or radius) or number of outlets of a catheter used for the infusion. The tip length of the catheter is preferably defined as the length in the longitudinal direction of the catheter of an in particular specifically formed portion which is located in particular at the distal end of the catheter and comprises outlets for the medical substance for exiting the catheter. The proximal end of the tip is divided from the rest of the catheter in particular by a step in the outer circumference which leads to a smaller diameter of the tip compared to parts of the diameter proximal of the step. The proximal end of the tip may also be defined as in particular the point at which the diameter of the catheter decreases in particular continuously or stepwise in the distal direction. The longitudinal extension of the catheter is in particular defined as the direction in which the medical substance is meant to flow through the catheter during an infusion. The distal end of the catheter is defined as the end at which the medical substance is meant to exit the catheter, the proximal end of the catheter is defined as the end at which the medical substance is meant to enter the catheter in order to be infused.

Alternatively or additionally, the geometric property is the position of a catheter which is used for infusing the medical substance. This position in particular is the position of the catheter relative to the target region and is for example determined by applying a medical imaging method to the patient's body when introducing the catheter. In this way, both the position in the anatomical body region at which the catheter shall be placed for the infusion and the trajectory along which the catheter may be lead during introduction to the patient's body may be determined. Preferably, the mentioned surface property of the infusion device is at least one of a surface roughness of an inner and/or outer surface of a catheter used for the infusion or topology (i.e., a three-dimensional surface geometry) of such a catheter.

According to another embodiment, the at least one physical parameter preferably is a physical parameter of the medical substance. Such a physical parameter of the medical substance in particular describes a fluid dynamic property of the substance. The fluid dynamic property preferably is at least one of pressure (in particular, fluid dynamic pressure), flow rate, flow velocity, fluid resistance, viscosity, stickiness, binding rate and density in (or of) the medical substance, or the molecular weight of an active substance, or concentration In particular, each of these physical quantities is considered for a state in which while the infusion takes place. Consequently, the physical parameter may also be the infused volume or mass of the medical substance which has been infused or shall be infused as a function of time, in particular calculated from flow rate, cross section of the infusion device and time.

Alternatively or additionally, the physical parameter (in particular as a physical parameter of the infusion setup) describes, in particular is, time, in particular time which has passed since starting the infusion while the infusion continues (i.e. the duration of the infusion), in particular since starting the infusion.

Preferably, spatial distribution data comprising spatial distribution information about the predetermined spatial distribution is acquired. The spatial distribution data preferably serves as a basis for generating the relationship data. The predetermined spatial distribution in particular is or describes a two- or three-dimensional concentration or flow pattern of the medical substance, in particular when applied to human tissue by using the infusion device. More particularly, the predetermined spatial distribution is defined or determined specifically for the infusion device. This predetermined spatial distribution preferably has a generic, non-patient-specific geometry and concentration profile or flow pattern profile. Physical parameters of the predetermined spatial distribution are preferably defined in analogy to the fluid dynamic physical parameters of the infusion setup. The term of geometry in this context encompasses both the shape, size (i.e. volume) and dimensions of the predetermined spatial distribution. A shape is in particular understood as the visual appearance of the predetermined spatial distribution, in particular more particularly its similarity to basic geometric shapes. The geometry, in particular the shape can be defined by a finite number (e.g. 1, 2, 3, 4, or 5, in particular less than 100 or preferably less than 10) of, at least one, preferably exactly (i.e. only) two geometric parameters, in particular at least one or exactly two geometric dimensions. Preferably, the spatial distribution describes a geometry which has a basic geometric shape or represents a superposition of bodies, in particular bodies of basic geometric shape (e.g. of a sphere and a cone or of two different ellipses). The superposition is in particular defined as the surface of the superposition being composed of those parts of surfaces of the bodies which are not inside one of the bodies of the superposition. Preferably, the basic geometric shapes are rotational solids such as in particular elements belonging to the species of ellipsoid (or more specifically, a sphere) cylinder or cone, in particular as being on of those species. The defining geometric dimensions of the predetermined spatial distribution in particular are the length of a semi-axis of an ellipsoid (more specifically, the radius or diameter of a sphere) or its surface area (in particular the surface area of a cone or an ellipsoid). Alternatively or additionally, the geometry, in particular the shape of the predetermined spatial distribution can be an envelope of the surface of, for example, intersecting spheres, the dimensions of which being defined by the respective radii. It is to be noted that a predetermined spatial distribution having the shape of a sphere is a spatial case of a bi-axial ellipsoid having two equal semi-axes (more particularly, a sphere may be said to be a uni-axial ellipsoid). In that spatial case, the predetermined spatial distribution may be said to be similar to a basic geometric shape which is defined by exactly one geometric parameter, namely the respective spherical radius. As further embodiments of a basic geometric shape, a box having at least two equal side lengths may be considered as a basic geometric shape which is defined by (exactly) one or two geometric parameters, depending on the number of equal side lengths. In the case of three equal side lengths, i.e. only one geometric parameter, the box is represented by the special case of a cube. According to an even further embodiment, the box may have three different side lengths and therefore be an example of a geometric shape which is defined by exactly three geometric parameters. Furthermore, the basic geometric shape may have cylindrical form which is defined by exactly two geometric parameters, namely the cylinder radius and the cylinder length. In the case of a cone, the basic geometric shape is defined by the length of the cone (i.e., the length of its longitudinal axis) and the radius of its bottom surface. The geometric parameters which define the shape of the predetermined spatial distribution more generally define its geometry, i.e. both its shape and its size (its volume). In this disclosure, an example of the invention is given for the case of an ellipsoidal shape. However, the disclosure may be applied correspondingly to other geometries, in particular other basic geometric shapes for a predetermined spatial distribution. In particular, where it is disclosed that the semi-axes of the ellipsoidal shape are acquired or determined in the method disclosed herein, the edge lengths of a rectangular volume such as a box or cube may be used as a geometric parameter instead of the semi-axes. Information about the predetermined spatial distribution, in particular the spatial distribution data, is contained preferably in a database comprising predetermined spatial distributions which have been determined, in particular calculated, based on the physical parameter as described above. As will be shown later, specific values of the geometric dimensions which define the geometry of the predetermined spatial distribution have an in particular empirically predetermined relationship with the physical parameter. Therefore, the aforementioned relationship information is or describes in particular a relationship between the physical parameter of the infusion setup and at least one geometric parameter of the predetermined spatial distribution.

The relationship between the physical parameter of the infusion setup and the predetermined spatial distribution in particular is a mathematical relation between the predetermined spatial distribution and the physical parameter. The mathematical relation is in particular based on physical, more particularly fluid dynamic, principles. Alternatively or additionally, the relationship is or comprises a more general dependency of the predetermined spatial distribution on the physical parameter (and vice versa) such as for example a correlation or a tendency. The correlation or tendency in particular describes a behaviour of the predetermined spatial distribution when the at least one physical parameter is varied. Information about their relation is preferably acquired outside of the method disclosed herein, in particular at a preceding point in time, based on calculating and simulating the infusion, in particular by using values from literature and collecting empirical data (in vitro or in vivo) and subsequent extrapolation or simulation.

The relationship information in particular describes a dependency of the geometry of the predetermined spatial distribution on the physical parameter. The geometry of the predetermined spatial distribution in particular has the general shape of an ellipsoid, more particularly a biaxial ellipsoid. In specific cases, the geometry may have the general shape of a tri-axial ellipsoid. A specific geometry of the predetermined spatial distribution may be achieved by different combinations of physical parameters of the infusion setup. It is to be noted that the at least one physical parameter may also have an effect not only on the geometry of the predetermined spatial distribution but also on fluid dynamic parameters of the medical substance in the predetermined spatial distribution. In particular, the concentration profile or the flow velocity of the medical substance within the region covered by the predetermined spatial distribution is influenced by the physical parameter of the infusion setup. Alternatively or additionally, the relationship information in particular is or comprises information about feasible, in particular clinically feasible, combinations of physical parameters of the infusion setup that lead to specific feasible parameters of the predetermined spatial distribution.

If the predetermined spatial distribution has an ellipsoidal shape, its spatial extent, in particular volume, is defined by two semi-axes a and b, where a generally is not equal to b. In specific cases, however, a may be equal or approximately equal to b. In that case, the predetermined spatial distribution has a spherical or approximately spherical shape. The absolute values or a and b and therefore also the ratio between a and b are influenced in particular by the physical parameter of the infusion setup. Specifically, they are influenced by the duration of the infusion. The exact mathematical relation between a and b in particular depends on physical parameters of the medical substance like for example molecular size and infusion rate, electrical charge of its constituents, half life of a radioactive agent and efflux rate of the medical substance towards the target region (which is in particular governed by the flow rate through the blood brain barrier in the case of the target region being part of the brain, also called "loss"). More generally, the shape of the predetermined spatial distribution is influenced by anyone of the physical parameters described above, in particular the flow rate of the medical substance in the infusion device, the infusion duration (i.e., time after starting the infusion) as well as hardware parameters relating to the infusion device such as a cannula step length or catheter tip length.

Preferably, target coverage data comprising target coverage information is acquired. The target coverage information describes, in particular constitutes or is, a planned (in particular, predicted) coverage of the target region by the medical substance. Within this disclosure, the term of information about the coverage encompasses information about the distribution of the medical substance in a two- or three-dimensional region of the patient's body, in particular in the target region. Preferably, information about the coverage also encompasses information about the distribution in the medical substance around the target region, in particular in healthy tissue, more particularly also in critical structures. The distribution of the medical substance is characterized by in particular the concentration of the medical substance in the respective region, more particularly also information about whether medical substance is present in the respective region or not. The distribution is further preferably characterized by the geometry of the coverage which is defined in particular in analogy to the geometry of the predetermined spatial distribution. The information about the coverage preferably also comprises information about a minimum dose of the medical substance in the target region which is necessary to achieve the treatment effect (also called therapeutic dose). In particular, the information about the coverage comprises information about a desired dose of the medical substance in the target region.

The position of the target region and off-target regions in the patient's body and their respective geometry is preferably determined on a patient-specific basis from medical image data which has been taken by application of at least one medical imaging method as defined above to the patient's body. Alternatively or additionally, the position and geometry of the target region and off-target regions may be acquired on a non-patient-specific basis from predetermined standard anatomical data, in particular an atlas.

An atlas typically consists of a plurality of generic models of objects, wherein the generic models of the objects together form a complex structure. The atlas of a femur, for example, can comprise the head, the neck, the body, the greater trochanter, the lesser trochanter and the lower extremity as objects which make up the complete structure. The atlas of a brain, for example, can comprise the telencephalon, the cerebellum, the diencephalon, the pons, the mesencephalon and the medulla as the objects which make up the complex structure. One application of such an atlas is in the segmentation of medical images, wherein the atlas is matched to medical image data, and the image data are compared with the matched atlas in order to assign a point (a pixel or voxel) of the image data to an object of the matched atlas, thereby segmenting the image data into objects.

Preferably, the information about the coverage also comprises information about at least one off-target region. Preferably, the maximum dose of the medical substance in an off-target region is set to zero, in particular if toxic effects are expected even with lowest doses or the cost of the medical substance prohibits wasting it outside the target region.

Preferably, the information about the coverage also comprises information about the outer spatial boundary of the distribution of the medical substance. In particular, the information about the coverage comprises information about whether the spatial distribution of the medical substance exactly or substantially exactly fits the geometry of the target region, is in particular at specific locations smaller than the target region or extends out of the target region. More particularly, the target coverage information comprises information about a basic geometric shape to which the coverage is most similar and about the characteristic dimensions of such a basic shape. For example, the target coverage information may comprise information which describes that the spatial distribution of the medical substance is similar to an ellipsoid which represents a basis geometric shape and additional information about the length of the semi-axes of that ellipsoid as representing the characteristic dimensions.

Preferably, infusion setup data comprising infusion setup information is determined. The infusion setup information in particular describes a planned infusion setup which shall be used for conducting the planned infusion. The infusion setup data is preferably determined based on the relationship and the target coverage data.

A particular overall goal of the inventive method is to optimise placement of a catheter used for direct delivery of the medical substance into the target region. The target region consists of or comprises in particular brain tissue. As noted above, the doses of the medical substance applied to the target region and off-target regions have to be optimised in view of medical requirements. Supposing the position of the catheter, in particular the catheter tip, in the patient's body, in particular relative to the target region, is known, in particular predetermined, such an optimisation is preferably based on the physical parameter of the infusion setup. The infusion setup information therefore preferably is or comprises the physical parameter of the infusion setup which has been determined such that the planned spatial distribution of the medical substance relative to the target region or off-target regions is optimised. The planned spatial distribution of the medical substance is a spatial distribution which results from determining the distribution of the medical substance based on in particular fluid dynamic computations or empirical data which use the physical parameter. The desired physical parameter is determined for example by a deterministic or probabilistic simulation of the relevant physical processes or selected from a database of predetermined physical parameters having a predetermined relationship to a predetermined spatial distribution. The respective predetermined spatial distribution is then used as the planned spatial distribution.

Preferably, the infusion setup information is determined based on a comparison of the planned spatial distribution of the medical substance relative to the target region and the planned coverage of the target region by the medical substance. In particular, the planned spatial distribution is determined to have a geometry of generally ellipsoidal shape which is characterized by semi-axes a and b. A generally ellipsoidal shape in the framework of this disclosure refers to any case of an ellipsoid, be it bi-axial or tri-axial or the special case of a sphere (i.e. a uni-axial ellipsoid). A substantially ellipsoidal shape in the framework of this disclosure refers to an ellipsoidal shape, in particular a bi-axial ellipsoidal shape in which one of the two semi-axes is preferably 20%, 30%, 50% or more (in particular, 1.5 times or two times) longer than the other semi-axes. In analogy, a substantially spherical shape may be defined as a uni-axial ellipsoid or a bi-axial ellipsoid in which one semi-axis is only slightly larger than the other semi-axis, in particular is less than 20% longer than the other semi-axis. The semi-axes a and b are examples of geometric parameters defining the shape, more generally the geometry, of the planned spatial distribution. The predetermined spatial distribution may thus be said to have at least substantially the shape, in particular exactly the shape, of a rotational solid, in particular a convex and/or closed rotational solid. Generally, the infusion device has an opening from which the medical substance is allowed to exit into body tissue (such as a catheter tip). The opening is approximately in the centre of the planned spatial distribution and the values of the length of the semi-axes a and b are determined by the physical parameter of the infusion setup, in particular by fluid dynamic parameters or empirically determined values. (In specific cases in which the opening is not in the centre or not approximately in the centre, an eccentricity, i.e. distance of the centre of the distribution to the opening, may be larger than zero and be used as an optimization parameter in accordance with this disclosure.) For example, a basic geometry of the predetermined spatial distribution may have ellipsoidal shape at a specific flow rate of medical substance. At a reduced flow rate, the shape may become more spherical, whereas an increased flow rate may lead to an elongation of the ellipsoid along the longitudinal direction of the catheter in the proximal direction. An increased duration of the infusion may lead to an extension of the ellipsoid compared to the basic geometry in a direction transverse to longitudinal direction of the catheter. The disclosed method therefore seeks to optimise a set of parameters comprising in particular at least the lengths of the semi-axes of the ellipsoid (or, more specifically, the ratio of their lengths to one another), the flow rate of the medical substance in the infusion device and the tip length of the catheter used for the infusion. The set of parameters is optimised such that a desired coverage of the target region and off-target regions with the medical substance may be achieved. The optimisation may also be conducted in consideration of different possible entry points for a catheter into the patient's body or trajectories which the catheter takes on its way from the entry point to its final location in the patient's body at which the medical substance is to be infused.

Relevant optimisation parameters preferably are also prioritized (i.e. sorted by their relevance which denotes an order in which the parameters are to be considered) by the inventive method. Criteria for prioritizing the optimisation parameters or the goals, the achievement of which depends on the optimization parameters, may include:

maximizing the coverage of the target (for example, by determining the percentage of the target into which the medical substance is or would be infused);

minimizing leakage of the medical substance outside of the target region (for example by determining the percentage of the medical substance that is or would be placed outside the target region);

minimizing the coverage of critical structures (for example by determining the percentage of critical structures that is or would be covered by medical substance);

maximizing the distance from the location of infusion to leakage pathways through which the medical substance may leak in particular in an undesirable manner (for example by considering the distance from the location of infusion to major blood vessels, major white brain matter pathways or spaces in which cerebrospinal fluid is present);

minimizing trajectory risks (which may be defined for example as the risk of a cannular used as an infusion device crossing a sulcus);

minimizing the total number of catheters to be used and/or maximizing the distance between individual catheters.

A goal of the optimisation in particular is to find an optimal treatment plan for conducting the infusion. Such a treatment plan in particular comprises patient information (in particular, information about the gender, age, body dimensions and mass as well as health state of the patient) and about the medical treatment to be conducted. The information about the medical treatment in particular is information about the cannular or catheter tip position, an entry position for entry of the infusion device into the patient's body, information about the medical substance to be infused, duration of the infusion, number of catheters etc.

The infusion setup data is in particular determined such that the infusion setup information comprises the physical parameter or physical parameters of the infusion setup for which the predetermined spatial distribution best fits the planned coverage of the target region. Preferably, target region geometry data is acquired which comprises target region geometry information. The target region geometry information describes, in particular is or constitutes the geometry of the target region as defined above. The target coverage data then preferably is acquired based on the target region geometry data. The target region geometry data is in particular acquired based on image information contained in medical image data taken for the specific patient or acquired from a database of non-patient-specific medical image data. The target region geometry information then serves as a basis on which the planned coverage of the target region may be described or determined.

A treatment plan is preferably determined based on the infusion setup data. In particular, the information contained in the treatment plan which relates to the manner in which the infusion is to be conducted is determined based on the physical parameter of the infusion setup which is contained in the infusion setup data. Alternatively, the infusion setup data may be determined based on a predetermined treatment plan. In particular, the physical parameter may be optimised in view of information contained in the predetermined treatment plan. In this alternative embodiment, the treatment plan therefore represents a boundary condition for optimisation of the physical parameter.

The appended description of the figures discloses embodiments of a workflow (i.e. a method) for generating such a treatment plan. That disclosure is herewith incorporated into the general part of the description by reference. The incorporated disclosure in particular is the description of FIGS. 11 to 13.

The common features of all three embodiments of the workflow for generating a treatment plan are the following:
  acquiring medical image information about the anatomical body parts of the patient to be treated;
  determining, based on the medical image information, the target region and off-target regions (in particular, critical structures);
  defining physical parameters to be optimised along with a range in which they shall be optimised and prioritising the physical parameters;
  acquiring information about limitations of the envisaged infusion treatment, in particular about hardware limitations of the infusion setup or anatomical/physiological limitations.

According to one embodiment of the workflow for generating a treatment plan, first a feasible trajectory for inserting an infusion device, in particular a catheter, which is to be preferably used is determined based on combined information. The combined information has been gathered by combining the medical image information, information about optimisation parameters and limitations. On the basis of information about the feasible trajectory, the associated physical parameters of the infusion setup, in particular fluid dynamic parameters such as flow rate, are determined. Then, a predetermined spatial distribution is selected which is associated with those physical parameters based on database, atlas-based or patient-specific predetermined information. The predetermined spatial distribution is then analysed as to a desired target coverage. If the target coverage is determined to be sufficient, the predetermined spatial distribution is used for simulating the envisaged infusion treatment, in particular kept for generating a proposed treatment plan. If it is determined that the target coverage is not sufficient, the predetermined spatial distribution is used as an initial distribution which shall be modified and re-evaluated as to a sufficient target coverage.

According to two other embodiments of the workflow for generating a treatment plan, first information about the predetermined spatial distribution is acquired based in particular on a characteristic dimension of in particular the target region, such as its diameter or circumference. The predetermined spatial distribution is then evaluated as to sufficiency of target coverage and if necessary modified as described with regard to the preceding embodiment of the workflow. If a final distribution of the medical substance is determined as a best fit, an associated trajectory is determined from the database of associated pairs of trajectories and spatial distributions of medical substance. The trajectory is then evaluated as to its clinical feasibility. If the trajectory is determined to be clinically feasible, both the finally determined spatial distribution and the trajectory are kept for use in a proposed treatment plan. In this case, the trajectory, in particular the trajectory associated with, in particular leading to the spatial distribution may be termed to be clinically feasible.

In other words, the predetermined spatial distribution according to one embodiment of the disclosed method is selected based on the target coverage data. In case the predetermined spatial distribution is selected from a relational database of predetermined spatial distributions and their relationships to the physical parameter, the selected predetermined spatial distribution may be adapted to fit the planned coverage. The adapted predetermined spatial distribution may then serve as a basis for determining the physical parameter, in particular by application of an inverse algorithm for evaluating fluid dynamic equations or by estimation of the physical parameter based on the formulae which describe the predetermined distribution. Similarly, the relationship data is preferably acquired based on selecting a predetermined spatial distribution which best fits the planned coverage.

In the following, example embodiments of the present invention are described with reference to the Figures, which are merely to be regarded as examples of the invention without limiting the invention to the specific embodiment, wherein:

FIGS. 10a and 10b show a mathematical relation for determining semi-axes of an ellipsoidal spatial distribution;

Figure 1:
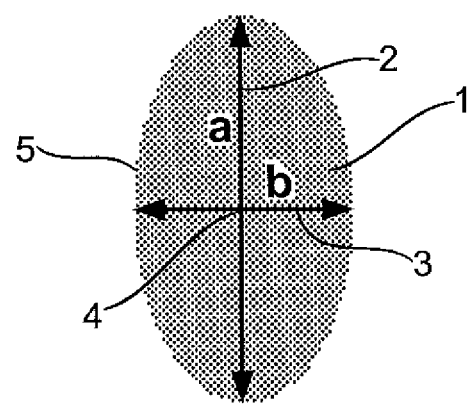
FIG. 1 is a basic representation of an ellipsoidal geometry of a predetermined spatial distribution.

FIG. 1 is a general depiction of the dimensions of an ellipsoid 1 having semi-axes a 2 and b 3. A semi-axis is defined to extend from the centre 4 of the ellipsoid to its circumference 5. The respective axes of the ellipsoid thus have a length equivalent to double the length of a corresponding semi-axis. The ellipsoid 1 shown in FIG. 1 is an example of the geometry of the predetermined spatial distribution.

Figure 2:
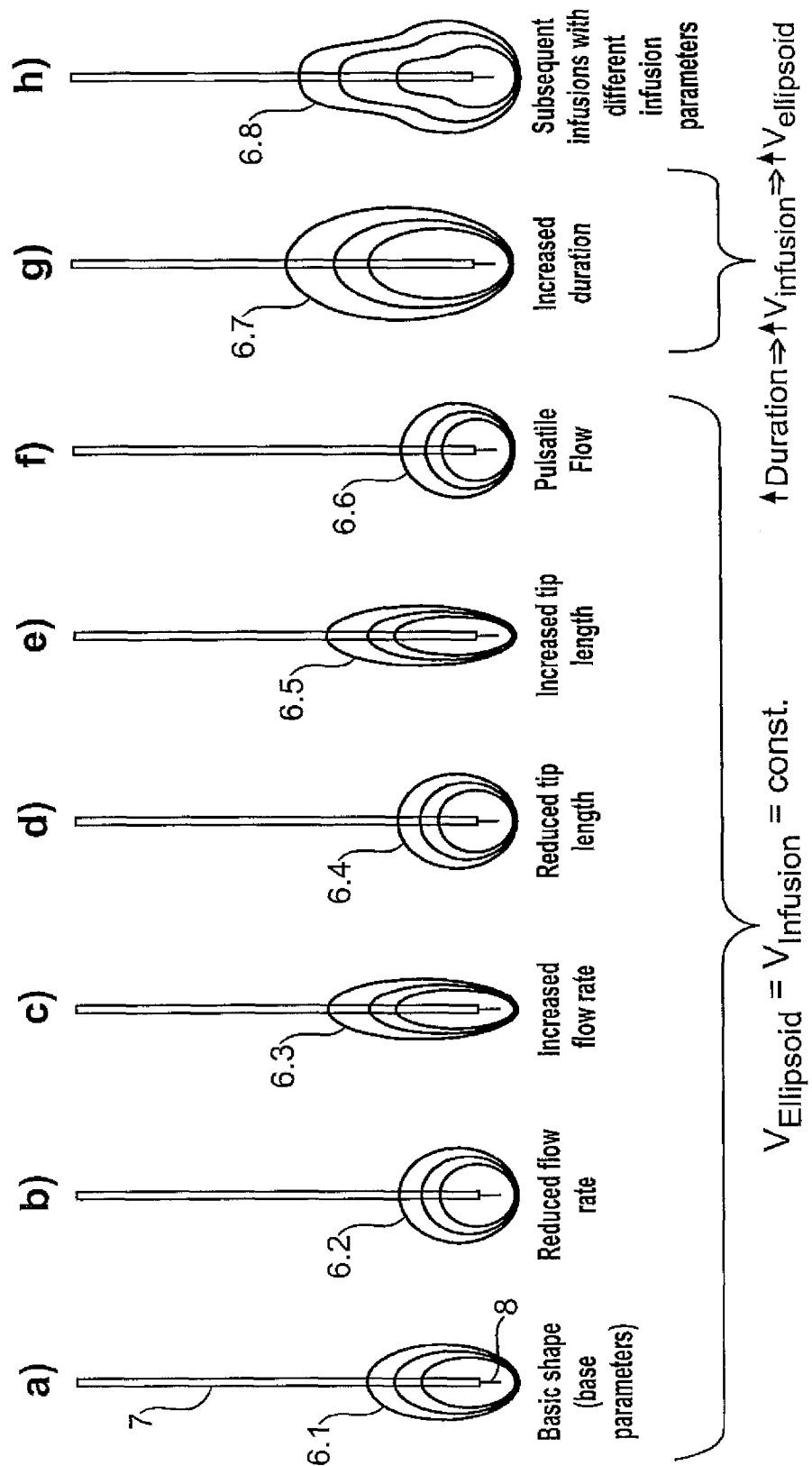
FIGS. 2a to 2h show example alterations of the ellipsoidal geometry in relation to qualitative changes of physical parameters.

FIG. 2 illustrates example graphical outputs of predetermined spatial distributions 6.1 to 6.8 which have been determined by simulation based on variations of different physical parameters. FIGS. 2b to 2f illustrate different predetermined spatial distributions which have been generated by variation of the physical parameter indicated below the illustration of the predetermined spatial distributions 6.2 to 6.6 when compared to a base parameter, based on which the basic shape of a basic predetermined spatial distribution 6.1 was generated (i.e. based on basic physical parameters) as illustrated by FIG. 2a. For the predetermined spatial distribution 6.1 to 6.6, the volume of the predetermined spatial distribution $V_{ellipsoid}$ is equal to the infusion volume $V_{infusion}$, i.e. the volume of the infused medical substance, which were both held constant for generating the predetermined spatial distribution 6.1 to 6.6. For generating the predetermined spatial distribution 6.7 of FIG. 2g, the infusion volume (equal to the volume of the predetermined spatial distribution) and the infusion duration (i.e. the time during which the infusion was run) were varied while keeping the other relevant physical parameters constant. The predetermined spatial distribution 6.8 of FIG. 2h illustrates an overlay of basic geometric shapes, for example an almost circular or spherical predetermined spatial distribution around the tip 8 of the catheter 7 which extends into a more elliptical or ellipsoidal shape towards the proximal end of the catheter 7. Such a predetermined spatial distribution 6.8 was achieved by running subsequent infusions with different physical parameters in a time interval short enough to generate the overlay of basic geometric shapes before older parts of the predetermined spatial distribution 6.8 (i.e. those parts generated during an earlier one of the subsequent infusions) could vanish e.g. by convection into the surrounding issue. The physical parameters varied for the simulations shown in FIGS. 2b to 2f were the flow rate (FIGS. 2b and 2c, reduced and increased, respectively, compared to the simulation of FIG. 2a), the length of the tip 8 of the catheters 7 (in FIGS. 2d and 2e, reduced and increased, respectively compared to the simulations of FIG. 2a), and a pulse of the flow of the medical substance (pulsed for the simulation of FIG. 2f compared to a continuous flow according to the simulation of FIG. 2a).

For all of FIGS. 2a to 2h, it becomes clear that the predetermined spatial distributions at the beginning of the infusion process extend around the tip 8 of the catheter 7. As a general tendency, it has been found that for a longer infusion time (cf. FIG. 2g), the spatial distribution of the medical substance extends more and more along the longitudinal direction of the catheter 7 in a proximal direction opposite to the flow direction of the medical substance in the catheter 7 away from catheter tip 8. This phenomenon is also called backflow along the catheter.

In FIG. 2b, the flow rate of the medical substance in the catheter 7 was reduced compared to the flow rate used in FIG. 2a. The result is that the predetermined spatial distribution 6.2 assumes a more sphere-like geometry compared to the predetermined spatial distribution 6.1 of FIG. 2a. A sphere-like shape comprises semi-axes a and b which are approximately equal. In contrast thereto, the term of an ellipsoidal distribution is directed to a geometry of the predetermined spatial distribution which has semi-axes a and b of an ellipsoid which are substantially not equal, in particular significantly different from one another. Therein, the longer semi-axis generally extends along the longitudinal direction of the catheter 7 (in particular in the case of a bi-axial ellipsoid). As may be seen from FIG. 2c, the predetermined spatial distribution 6.3 which was generated by increasing the flow rate compared to FIG. 2a deforms the predetermined spatial distribution 6.1 into a more ellipsoidal geometry which extends further proximally along the catheter 7 than it does in FIG. 2a.

FIG. 2d represents a predetermined spatial distribution 6.4 which has been determined for a reduced length of the tip 8 of the catheter 7 than was simulated for FIG. 2a. The result is that the longitudinal semi-axis (which is defined to extend in the longitudinal direction of the catheter 7) of the predetermined spatial distribution 6.4 is shorter than for the basic shape shown in FIG. 2a. The cross-section of the predetermined spatial distribution 6.4 appears to be more oval (i.e. more elliptical) than that of the predetermined spatial distribution 6.1.

FIG. 2e shows a predetermined spatial distribution 6.5 which has been generated using a catheter 7 having a tip length which is longer than that of the tip 8 used for the simulation of FIG. 2a. The result is that the predetermined spatial distribution 6.5 has a longitudinal semi-axis which is longer than that of the predetermined spatial distribution 6.1, while having a shorter transverse semi-axis (which is defined to extend in a direction transverse, i.e. perpendicular to the longitudinal direction of the catheter). As a general rule it is to be noted that, if the longitudinal axis is longer, the transverse axis is shorter (and vice versa) to achieve the same distribution volume, i.e. volume of the predetermined distribution. A tendency may thus be determined that, with an increase in flow rate or length of the tip 8 of the catheter 7, the longitudinal semi-axis of an ellipsoidal predetermined spatial distribution is increased, while the length of the transverse semi-axis is decreased. Thus, an increase in catheter tip length or flow rate leads to a more ellipsoidal distribution. A reduction in flow rate or catheter tip length leads to a more spherical distribution, i.e. to a shorter longitudinal semi-axis and a longer transverse semi-axis until a minimum aspect ratio of 1 is reached. In particular, a variation of flow rate or catheter tip length leads to a variation in the aspect ratio of the axis of the predetermined spatial distribution (in the case of an ellipsoidal predetermined spatial distribution, a change in the aspect ratio of the length of the longitudinal semi-axis to the length of the transverse semi-axis) while the volume of the predetermined spatial distribution remains constant.

For the example of FIG. 2h, the infusion was conducted with a low infusion rate at the beginning of the infusion, then increased for a certain interval, at the end of which interval the spherical distribution generated at the beginning of the infusion has not yet moved into the surrounding tissue. In particular, the infusion rate may then be decreased again in order to maintain the initial spherical distribution and again increased in order to maintain the more ellipsoidal distribution. In that manner, the infusion rate may be switched between periods of high infusion rate and low infusion rate in order to generate a superposition of ellipsoids for the predetermined spatial distribution. The superposition of basic geometric shapes in the predetermined spatial distribution 6.8 can also be defined to be a superposition of subsequent spatial distributions which do not coexist at the same time or (only) during a time interval. In particular, the superposition is defined to be an integral (mathematical) of (optionally subsequent) spatial distribution over the time (during which the infusion of the medical substance is performed). In particular, the spatial distribution is a function of time and changes in particular with time.

Figure 3:
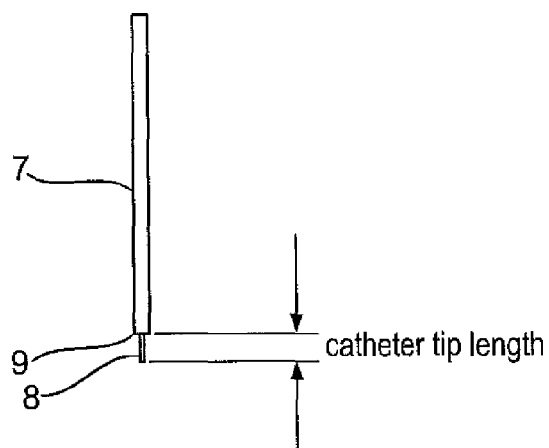
FIG. 3 shows a definition of the catheter tip length.

FIG. 3 shows a definition of the length of the catheter tip 8 of a catheter 7 used for conducting the infusion to be planned. As can be seen from the figure, the catheter tip is defined as the part of the catheter which extends between the distal end of the catheter and a step 9 which marks the end of a proximal portion of the catheter 7 having a larger cross-section and the beginning of the catheter tip 8 which has a smaller cross-section. The length of the catheter tip 8 is defined as the longitudinal length of the part of the catheter 7 having a smaller cross-section.

Figure 4:
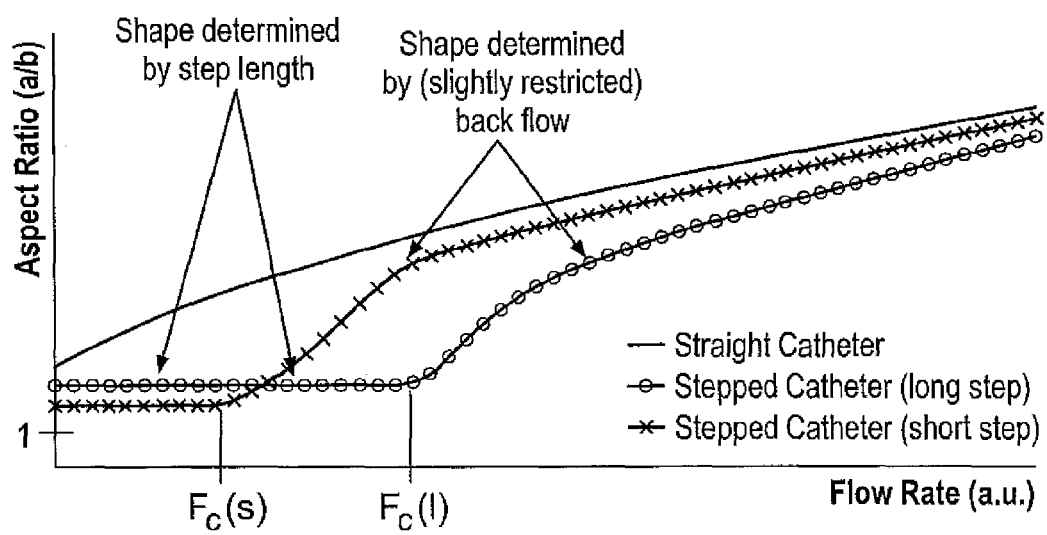
FIG. 4 shows a dependency of the aspect ratio of the ellipsoidal geometry on the flow rate of the medical substance.

FIG. 4 is a diagram showing a dependency of the aspect ratio of the ellipsoidal geometry of the predetermined spatial distribution of the flow rate of the medical substance. The aspect ratio is defined as a ratio between the semi-axes a and b of the ellipsoidal distribution of the medical substance and may be expressed as a/b or its inverse value. The three curves shown in FIG. 4 illustrate simulation results for the flow rate through the catheter in dependence on the aspect ratio and were taken for a straight catheter, a stepped catheter with a long step and a stepped catheter with a short step, respectively. The length of the step denotes the length of the catheter tip, i.e. the top curve was taken with a straight catheter, the lower curve with a catheter having a comparatively long catheter tip and the middle curve with a catheter having a comparatively short catheter tip. For a straight catheter, it has been found that the aspect ratio of the ellipsoidal geometry continuously rises with rising flow rate. Furthermore, among the three curves shown, use of a straight catheter leads to generally the most ellipsoidal shape. For the catheters having a stepped catheter tip, it has been found that the geometry is substantially constant displaying a constant aspect ratio for flow rates between zero and $F_c(s)$ denoting a critical flow rate for the short catheter tip and $F_c(1)$ denoting a critical flow rate for the long catheter tip, at which the aspect ratio starts to continuously increase with increasing flow rate. For values of the flow rate up to the critical flow rate, the geometry of the predetermined spatial distribution is generally determined by (only or predominantly) the length of the catheter tip, wherein the catheter having a longer catheter tip leads to a geometry of the predetermined spatial distribution which has been distorted away from a spherical geometry towards an ellipsoidal geometry—compared to the catheter having a shorter catheter tip. Furthermore, the critical flow rate for the catheter having a long tip is higher than the critical flow rate for the catheter having a short tip. For a flow rate larger than the respective critical flow rate, the geometry of the predetermined spatial distribution is determined more by the backflow and takes a more ellipsoidal geometry with rising flow rate. The influence of the catheter tip length on the aspect ratio for flow rate values larger than the respective critical flow rate appears to be smaller than the influence exerted by the backflow.

Figure 5:
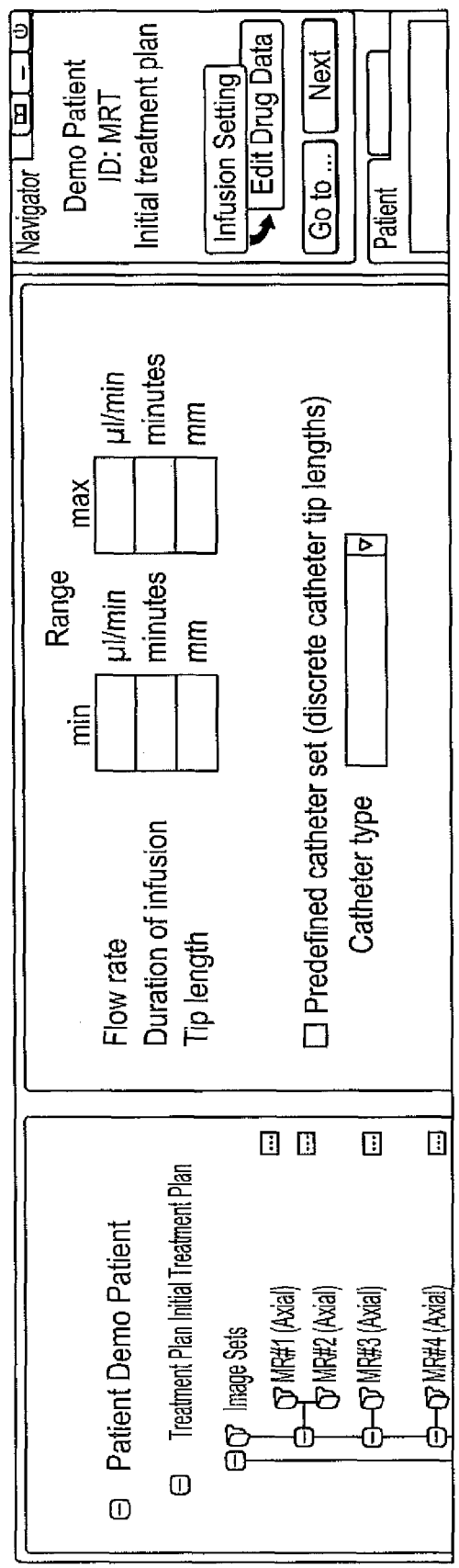
FIG. 5 shows a user interface for defining ranges of visible physical parameters.
Figure 6:
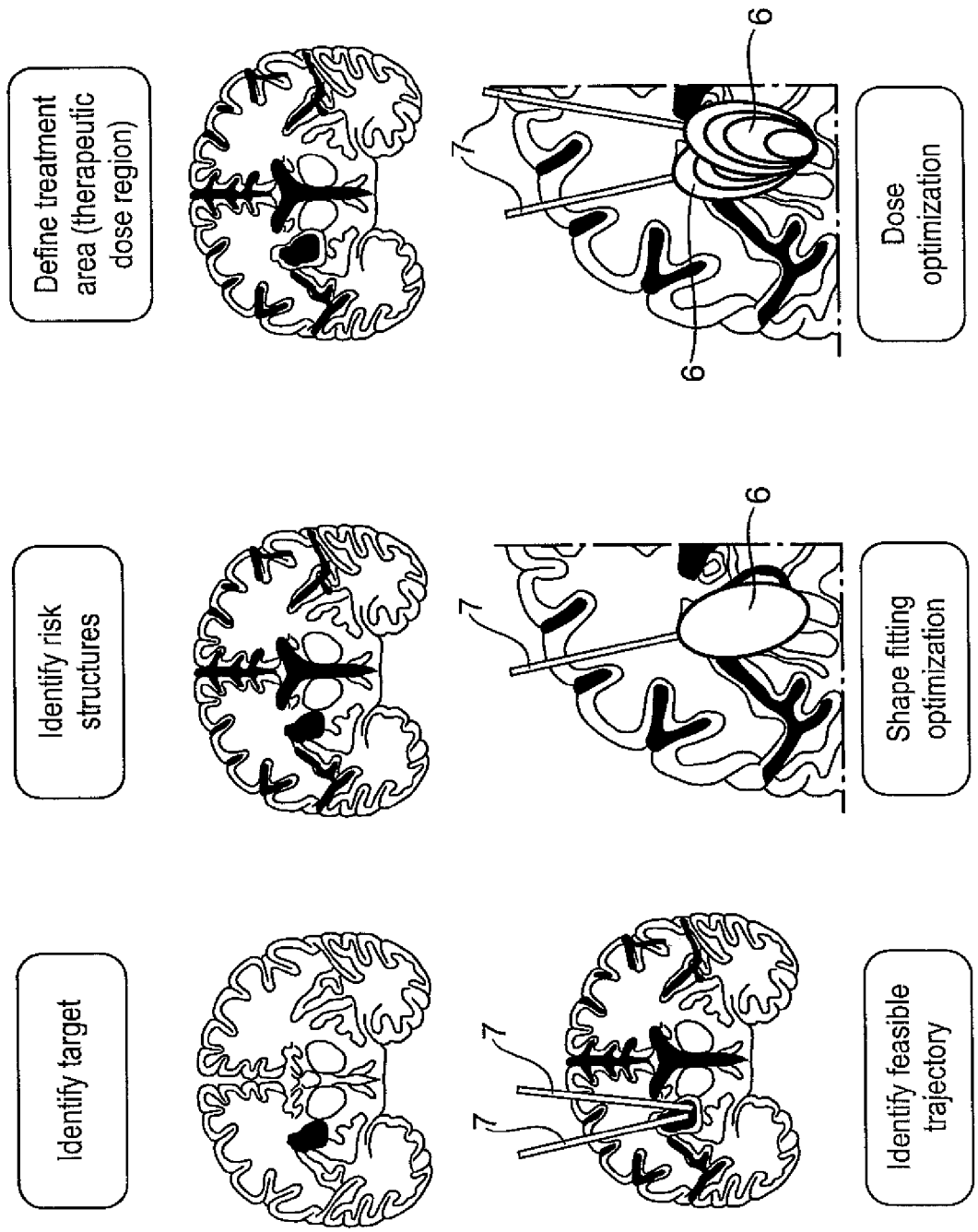
FIG. 6 shows medical image data which is used for treatment planning.

FIG. 5 shows a graphical user interface (GUI) generated by a software application used for the inventive infusion planning method. The GUI supports planning an infusion for a specific patient (in this case "DemoPatient") based on different sets of medical images ("image sets") which in this case were taken from different perspectives relative to the patient's body. Their respective medical images are shown in FIG. 6 which shows magnetic resonance (MR) image information for the human brain which is used to identify the target region, risk structures and define a treatment area, i.e. a region in the brain in which a therapeutic dose of the medical substance is to be distributed. The image information is used to identify a feasible trajectory (designated by the possible positions of the catheter 7 in the lower left part of FIG. 6) through which a catheter used for introducing the medical substance may be lead towards a location from which infusion or injection of the medical substance towards the treatment area is feasible. The treatment area comprises in particular the target region, and preferably also extends over the target area so as to surround it rather than exactly fitting the target region. In a step of shape fitting optimisation, a predetermined spatial distribution of the medical substance is layed over the graphical representation of the treatment area as a basic geometry (equivalent to a basic geometry as shown in FIG. 2*a*). Then, the GUI of FIG. 5 may be used to input predetermined ranges of physical parameters, in this case the flow rate, duration of infusion and catheter tip length, by entering their minimum and maximum values. Furthermore, the GUI offers a possibility for choosing a specific, in particular predetermined catheter type. In dependence on the information entered into the GUI of FIG. 5, the dose optimisation step of FIG. 6 continues with determining a coverage of the treatment area, in particular the target region, which would be achieved with an infusion using the physical parameters defined in FIG. 5. In the embodiment of FIG. 6, a second trajectory for simultaneously using a second catheter is also determined and a corresponding second coverage of the treatment area is determined and displayed simultaneously to the aforementioned coverage achieved by using the first catheter.

Figure 7:
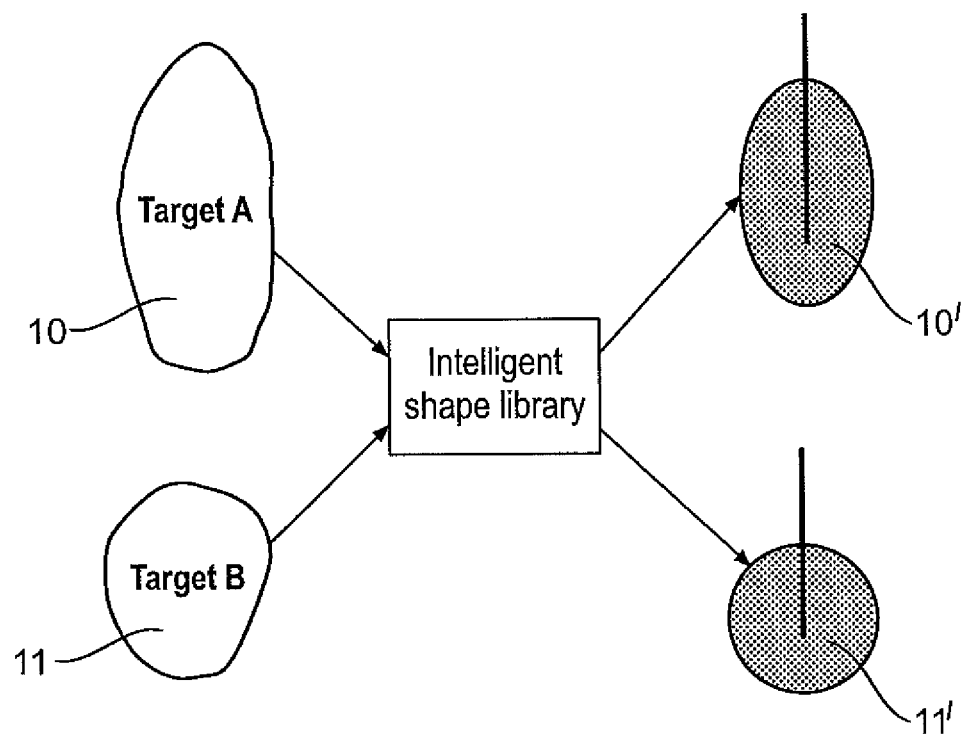
FIG. 7 shows the functional principle of an intelligent shape library.

FIG. 7 is a diagram showing the principles of an intelligent shape library which is preferably used for implementing the disclosed method of infusion planning. Depending on the geometry of a target region 10, 11, the intelligent shape library which is constituted in particular by the aforementioned relational database provides information on which predetermined spatial distribution 10', 11' would in principle fit the respective geometry of the target region 10, 11 best as an initial predetermined spatial distribution 10', 11' for conducting the simulation of the infusion while minimizing computation effort. The geometry of the target region 11 display a more spherical cross-section than the geometry of the target region 10. Correspondingly, the initial predetermined spatial distribution 11' has a more spherical shape than the rather ellipsoidal predetermined spatial distribution 10'. The initial predetermined spatial distribution 11' is therefore suitable for a simulation of the infusion for target region 11. Consequently, the predetermined spatial distribution 10' is preferably used for a simulation of an infusion for the target region 10 which displays a more elliptical cross-section.

Figure 8:
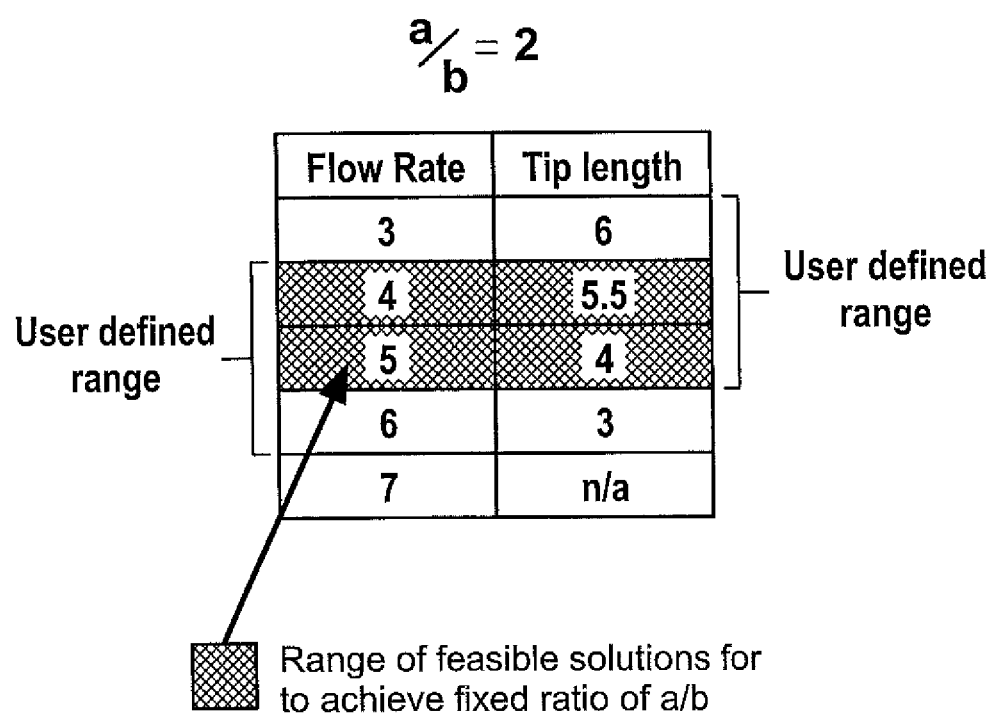
FIG. 8 shows a user-defined range of physical parameters for achieving a specific ratio of semi-axes a and b.

FIG. 8 illustrates a table of normalized values of flow rates in the catheter and associated tip lengths as are advantageously included in the relational database. The values marked as a user defined range are those values which correspond to the range entered into the GUI of FIG. 5. Since it is preferred that the predetermined spatial distribution of the medical substance remains constant, in particular that the aspect ratio of a/b remains constant during the entire duration of the infusion, the relational database contains additional information about flow rates and associated values of tip length which in combination support keeping the aspect ratio constant. This supports to avoid diffusion of the medical substance into in particular off-target regions. In the illustration of FIG. 8, these associated values of flow rates and tip lengths marked by a grey shading and termed "feasible solutions". A software application (i.e. a program) used for implementing the disclosed method of infusion planning then preferably provides a selection interface for selecting an associated pair of flow rate and tip length for simulating the envisaged infusion treatment. Alternatively or additionally, the software application may automatically determine a feasible solution. Associated value pairs which were contained in the user-defined range entered into the GUI but however do not constitute feasible solutions will not be suggested or selected by the software application. In the embodiment of FIG. 8, the aspect ratio is set to a/b=2 which serves as a boundary condition for determining the feasible solutions.

Figure 9:
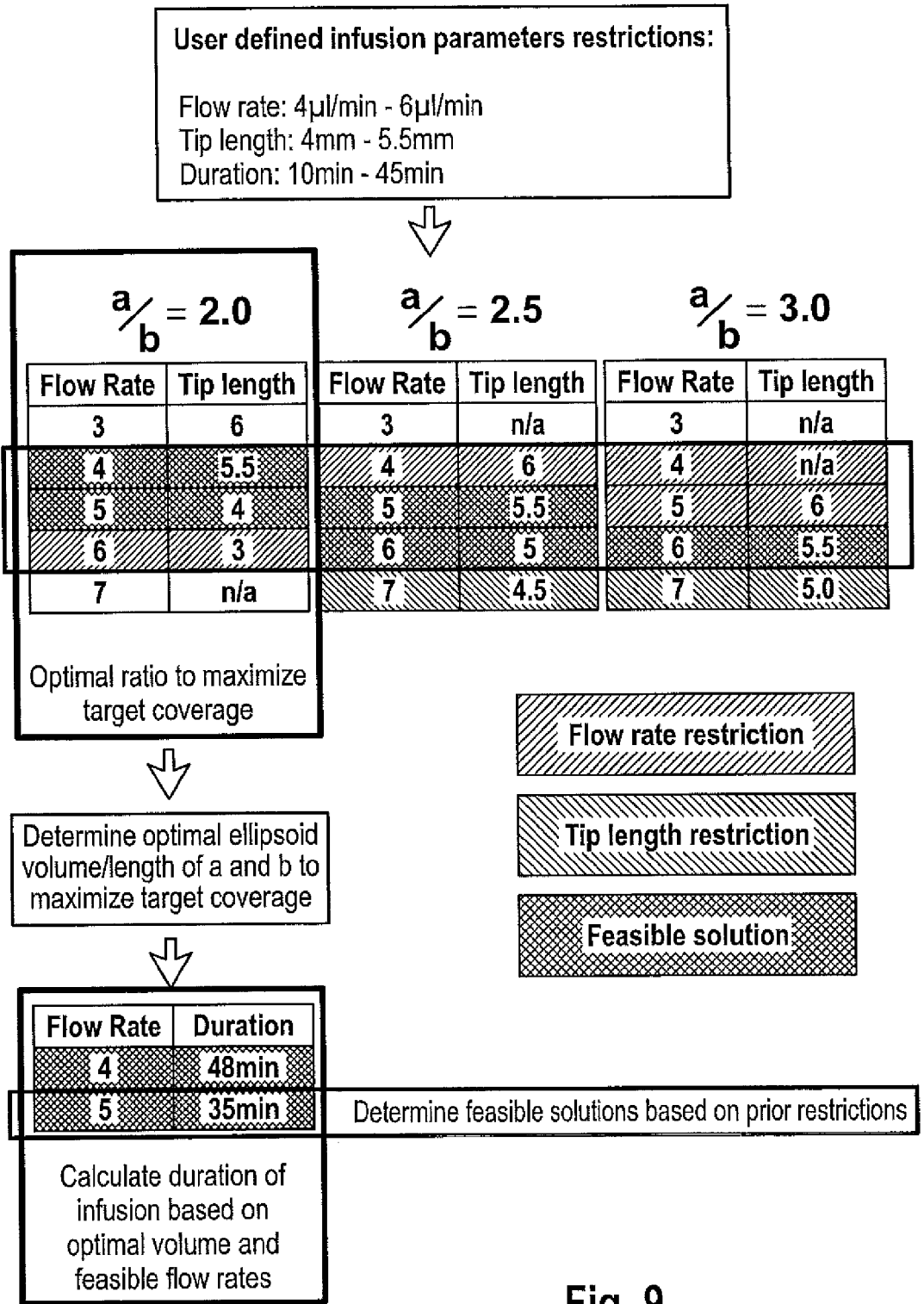
FIG. 9 shows an example of a shape library used for determining feasible physical parameters based on user-defined restrictions.

FIG. 9 shows a further embodiment of a user interface for defining the feasible range of physical parameters. The user again enters ranges of physical parameters (in particular, flow rate, catheter tip length and infusion duration) which are used as conditions for determining the feasible solutions. Tables of associated pairs of flow rate and catheter tip length are provided for different predetermined aspect ratios a/b=2.0 or 2.5 or 3.0. From these sets of associated pairs of values, the feasible solutions are determined for the optimal aspect ratio which best fits in this case to maximize the target coverage. According to the different shadings, the associated value pairs of flow rate and catheter tip length are further classified as either being restricted due to flow rates available for different catheter tip lengths due to hardware limitations, as tip lengths not being available due to lack of corresponding catheter hardware or as feasible solutions which denote associated value pairs which are in principle possible. The latter may be based on the condition that the catheters having the respective tip length are suitable for use with the respective flow rate. Starting from the aspect ratio and feasible solutions contained in the associated table of flow rates and tip lengths, the geometry, in this case the ellipsoid, of the predetermined spatial distribution is optimised in consideration of all available parameters such that the target coverage is maximized. The values of flow rate and infusion duration associated with such optimised parameters are then output. These values support to apply an optimal volume of the medical substance in view of the envisaged treatment effect while maintaining feasible flow rates.

Figure 10A:
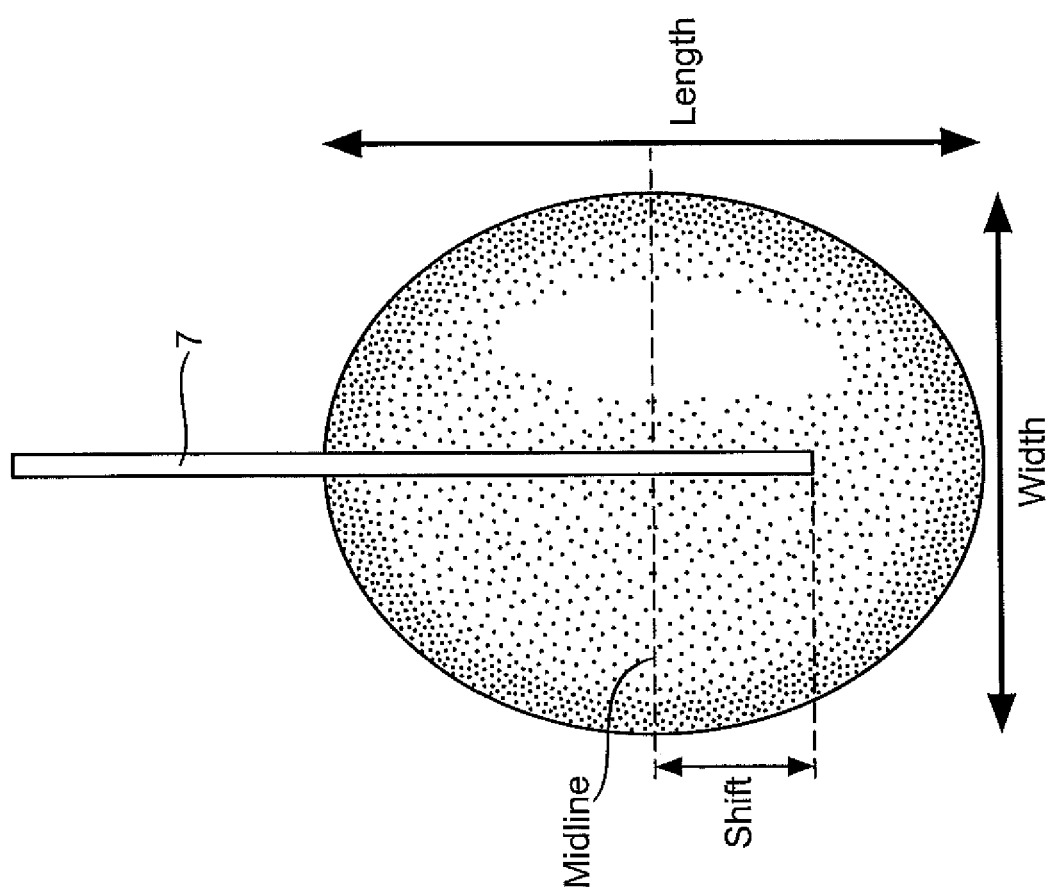

FIG. 10a gives an illustrative definition of the dimensions of a predetermined spatial distribution having a generally ellipsoidal geometry. The midline defines the line along which the transverse semi-axis is located. The shift denotes a distance between the distal end of the catheter tip and the midline. The length defines the length of the longitudinal semi-axis of the predetermined spatial distribution. The width defines the length of the transverse semi-axis of the predetermined spatial distribution.

FIG. 10b describes the principles of an algorithm for determining the geometry of the predetermined spatial distribution in dependence on the dimensions defined by FIG. 10a. In particular, a distance between the catheter tip and the centre of the predetermined spatial distribution may be determined using the disclosure of at least parts in particular FIG. 10b. The absolute numerical values of the physical parameters mentioned in FIG. 10b are not of general importance, rather normalised values will suffice for the algorithm to function. It is assumed that the distribution is shaped as a slight ellipsoid (i.e. a longitudinal spheroid) which is oriented along the main axis of the canular or catheter 7, i.e. the longitudinal axis of the ellipsoid lies on the longitudinal axis of the canular or catheter 7. The variables x and y are the length of the transverse and longitudinal axes of the ellipsoid. The equations for x and y define whether each point in image space (x, y) is in the ellipsoid or not in the ellipsoid. The volume of the spatial distribution of the medical substance scales linearly with the volume of medical substance infused through the infusion device. Vi is the infusion volume. This is the volume of medical substance infused through the infusion device and is typically measured directly on the infusion pump or along the infusion line. Vd is the distribution volume, the volume of medical substance in the brain. Vd is always greater than Vi because some space in the brain is taken up by cells and blood vessels etc. The letter p should be a "pi" symbol denoting the value of π=3,14159 . . . . The term of anisotropy defines the aspect ratio of the predetermined distribution. It is further assumed that the position of the distal end of the catheter (i.e. of the tip) relative to the centre of the predetermined spatial distribution (termed "shift" in FIG. 10a) is constant. The term "tip" in the equation for calculating the shift according to FIG. 10b denotes the tip length, i.e. the length of the catheter tip between its distal (open) end and the step (or other increase in diameter), whereas the term "length" denotes the length of the longitudinal axis of the predetermined spatial distribution (cf. FIG. 10a). Thus, the "shift" is a ratio described by a dimensionless numeric value. The relation shown in the box at the lower right half of FIG. 10b stipulates that the left-hand term of anisotropy, length, shift, x and y has to be less than a normalised numeric value of ¼. The graphical output in the upper right-hand half of FIG. 10b shows that the volume of the spatial distribution scales linear with the infusion time. Such knowledge may be used in order to optimise infusion time (which is synonymous to infusion duration). The colour bar for the volume of the distribution is normalised to minutes of infusion duration.

The teaching of FIG. 10b may be summarised as follows: Once the desired ellipsoid shape and location has been established, the tip location needs to be calculated using (library) knowledge of the tip location relative to the ellipsoid. The example shown here suggests a shift of 0.16 because experimentally we have found the tip to be ⅔ of the way through the infusion along the longitudinal axis of the catheter or cannula (and 0.66−0.5=0.16).

Figure 11:
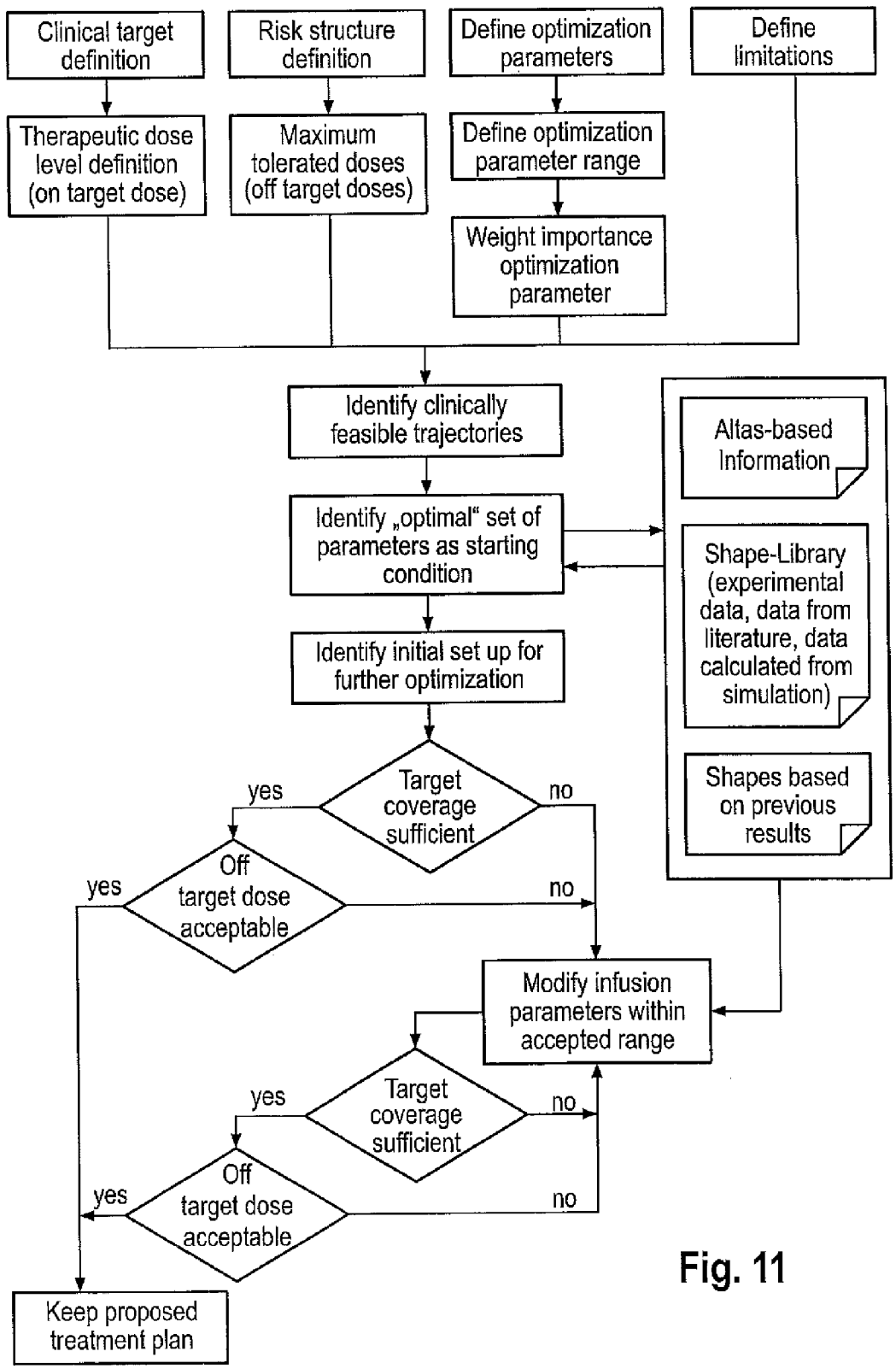
FIG. 11 shows a first embodiment of a treatment planning workflow.
Figure 12:
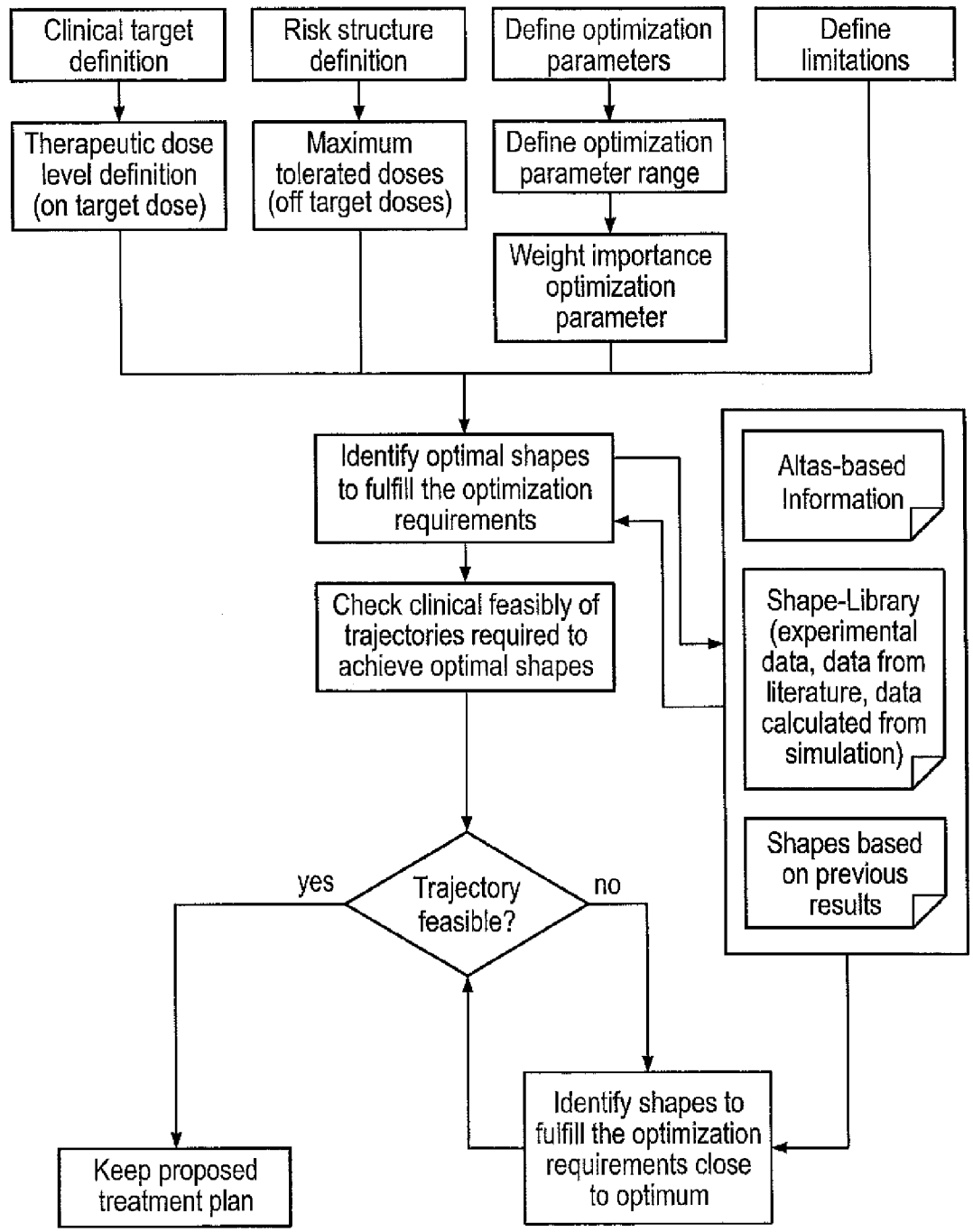
FIG. 12 shows a second embodiment of a treatment planning workflow.
Figure 13:
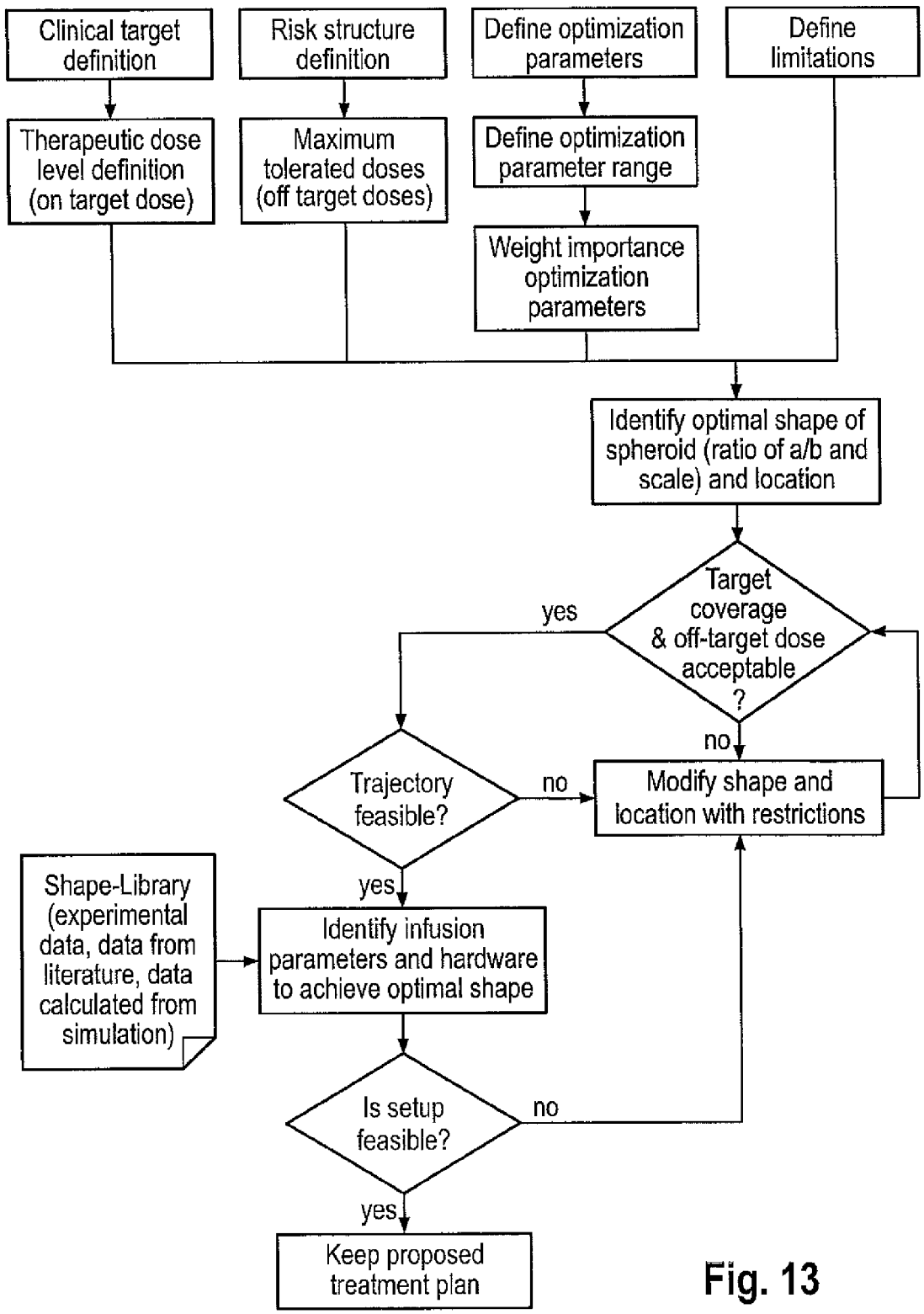
FIG. 13 shows a third embodiment of a treatment planning workflow.

FIGS. 11 to 13 show different embodiments of a treatment planning workflow which are associated with the infusion planning method as disclosed herein.

FIG. 11 shows a first embodiment of the treatment planning workflow. In step S1, medical image data of the patient's body is acquired and the clinical target, i.e. the target region, is defined, for example by manual interaction of a user who uses a pointing tool such as a mouse or a touch screen for marking the target region in the medical image information. Furthermore, risk structures, i.e. critical regions, are defined in the medical image information in a similar manner. The optimisation parameters defined by acquiring the ranges of the physical parameters entered into the GUI of FIG. 5. Furthermore, information about limitations are acquired. The limitations may be defined by hardware limitations of the infusion setup or limitations regarding the trajectories along which a catheter may be inserted. Step S1.1 continues with acquiring information about a therapeutic dose level, i.e. a dose of the medical substance to be applied to the target region in order to achieve a therapeutic effect, based on the information about the target region delimited in the medical image information. Similarly, information about a maximum tolerated dose which may be applied to off-target regions, in particular the critical structures, is acquired based on the definition of critical structures in step S1. Furthermore, step S2.1 includes defining an optimisation parameter range, i.e. a range in which the physical parameters acquired in step S1 are to be optimised. In step S1.2, the different physical parameters are weighted according to their importance, i.e. ordered according to relevance as described above.

Based on the information acquired in steps S1, S1.1 and S1.2, step S2 continues with identifying clinically feasible trajectories along a catheter is desirably inserted in order to support the desired target coverage. An optimal set of physical parameters for each of the feasible trajectories identified in step S2 is identified as a starting condition for the optimisation of the physical parameters in step S3. Steps S4.1, S4.2, S4.3 then describe three independent alternatives of acquiring information about predetermined spatial distributions. According to step S4.1, the information may be acquired based on atlas-based information. According to step S4.2, the information may be acquired based on a shape library (i.e. database), the data of which may have been generated based on data gathered from experiments or literature or from simulations. According to step S4.3, the information may be acquired based on previous results received from the specific patient who is to be treated, in particular based on medical image information about that patient's body or other information which has been gathered in connection with treatment of that specific patient.

The method then continues with step S5 which identifies based on the information gathered in step S3 and at least one of steps S4.1, S4.2 and S4.3 an initial infusion setup which is to be further optimised. The optimisation of the initial infusion setup, in particular of its physical parameter or physical parameters then essentially starts in step S6 in which a maximum target coverage is determined based on the initial infusion setup taking into account anatomical, pathological, clinical or infusion setup hardware limitations. The initial infusion setup also comprises information about the clinical feasible trajectories. This information may be used to vary the physical parameters until values of the target coverage meet the previously defined optimisation criteria. In particular, step S6 evaluates whether the target coverage is sufficient or not.

If step S6 evaluates that the target coverage is sufficient, the workflow continues with step S7 which evaluates whether the off-target dose, i.e. the dose of the medical substance administered to off-target regions, is acceptable. If step S6 determines that the target coverage is not sufficient, the optimisation procedure continues with modifying the physical parameters within an accepted range, in particular within the previously defined range, in step S8.

If step S7 determines that the off-target dose is acceptable, the initial infusion setup is kept for a proposed treatment plan which is to be used for conducting the envisaged infusion. If step S7 determines that off-target dose is not acceptable, step S8 is entered. After the physical parameters have been modified in step S8, the workflow then continues with step S9 which determines whether the target coverage is sufficient when using the modified physical parameters. If this is the case, step S10 is entered which determines whether the off-target dose is acceptable. If the target coverage determined in step S9 is not sufficient, step S8 is entered again.

If step S10 determines that the off-target dose is acceptable, the workflow leads to step S11 which determines that the infusion setup comprising the modified physical parameters shall be kept for the proposed treatment plan. If step S10 determines that the off-target dose is not acceptable, step S8 is entered again.

FIG. 12 shows a second embodiment of the workflow for determining the treatment plan which is based on the disclosed method of planning and infusion. Steps S10, S10.1 and S10.2 are equivalent to steps S1, S1.1 and S1.2 of FIG. 11, the respective description therefore not being repeated in the context of FIG. 12.

After step S10.2 has been executed, the method of FIG. 12 continues with step S11 which combines the information gathered in steps S10, S10.1 and S10.2 in order to identify an optimal geometry of the predetermined spatial distribution which fulfils the optimisation requirements. Information about the geometry of the predetermined spatial distribution is gathered in steps S12.1, S12.2 and S12.3 which are equivalent to steps S4.1, S4.2 and S4.3 of FIG. 11.

The optimal geometry of the predetermined spatial distribution identified in step S11 is used as a basis for checking, in step S13, the clinical feasibility of trajectories which would be required to achieve the optimal geometry of the predetermined spatial distribution.

The workflow of FIG. 12 then continues with step S14 which checks whether the trajectories are feasible. If this the case, the workflow continues with step S16 and the predetermined spatial geometry and the determined trajectories are kept for a proposed treatment plan. If step S14 determines that these trajectories are not feasible, the workflow enters step S15 which again acquires the information about predetermined spatial distributions which are close to fulfilling the optimisation requirements according to steps S12.1, S12.2 and S12.3. The method then continues with step S14 which uses the newly acquired information about the geometry of the predetermined spatial distribution for checking whether the trajectories associated with that geometry are feasible.

FIG. 13 shows a third embodiment of a workflow generating a treatment plan based on the disclosed method for planning an infusion.

Steps S20, S20.1 and S20.2 are again executed in the same manner as steps S1, S1.1 and S1.2 of FIG. 11. The information gathered in those steps is combined in step 21 to identify an optimal geometry of the predetermined spatial distribution, in particular an optimal aspect ratio and scaling as well as location in the medical image information onto which the predetermined spatial distribution is to be placed, in particular to be overlaid with the target region. The term of scaling refers to the total volume of the distribution. The ellipsoid is defined by the aspect ratio (a/b) and the volume (the length of a and b).

Step S22 then continues with determining whether the target coverage and in particular also the off-target dose achieved by selection and placing of the predetermined spatial distribution in step S21 is acceptable. If this is the case, step S23 checks whether trajectories for placing a catheter which lead to the location of the placed predetermined spatial distribution are feasible.

If steps S22 or S23 determine that either the target coverage or off-target dose or the trajectories are not acceptable of feasible, the workflow enters step S24 in which the geometry of the predetermined spatial distribution and the location at which it is placed are modified by respecting restrictions such as boundary conditions imposed by the location of critical structures or hardware limitations. After step S24, the workflow enters again into step S22, wherein the modified predetermined spatial distribution is then evaluated.

If step S23 determines the trajectories are feasible, the workflow continues with step S25 which determines physical parameters and in particular also the hardware constituents of the infusion setup which are needed to achieve an optimal predetermined spatial distribution. Based on the aspect ratio, scale and preferably also location determined in step S21, step S25 acquires in parallel step S26 information from a database of predetermined spatial distributions in analogy to step S4.2 of FIG. 11. In step S27 it is then determined whether an infusion setup based on the predetermined spatial distributions acquired in step S26 is feasible. If this is not the case, the method enters again into step S24 which then returns to step S22. If step S27 determines that the infusion setup is feasible, step S28 then determines to keep the infusion setup for a proposed treatment plan.

Throughout FIGS. 11, 12 and 13, the term of "shape" is also used for the predetermined spatial distribution. The shape-library illustrated by step S4.2 (and, in analogy, steps S12.2 and S26) corresponds to the above-described database containing information about predetermined spatial distributions.

An overlay of the predetermined spatial distribution over the image information acquired by steps S1, S10 and S20, which takes place in particular in steps S3, S11, and S25 is performed in particular by mapping geometry information or image information about the predetermined spatial distribution to the medical image information, in particular to image information about the target region. An optimal selection of an initial predetermined spatial distribution which is to be modified may be implemented alternatively or additionally. Such an optimal selection is preferably based on information about a characteristic dimension of the target region, such as its diameter or circumference. Such information about the characteristic dimension may be gathered for example automatically by a segmentation process carried out on the medical image information. Mapping of the predetermined spatial distribution to the medical image information is done preferably by an image fusion procedure.

As can be seen from the above description regarding FIGS. 11, 12 and 13, the embodiment of FIG. 11 relies on first determining a feasible trajectory, on the basis of which the associated physical parameters, in particular fluid dynamic parameters, are determined. Then, a predetermined spatial distribution is selected which is associated with those physical parameters and evaluated with regard to a desired target coverage. According to FIGS. 12 and 13, information about the predetermined spatial distribution is first acquired based in particular on the aforementioned characteristic dimension (in particular of the target region), and an associated trajectory is then evaluated as to clinical feasibility.

The invention claimed is:

1. A data processing method for planning an infusion of a medical substance into a target region of an anatomical body part, wherein the medical substance is to be infused using an associated infusion setup comprising the medical substance and an infusion device for performing the infusion, the method comprising:

acquiring, on a non-patient-specific basis from an associated atlas storing predetermined standard anatomical data, target region geometry data, the target region geometry data comprising target region geometry information describing a position and a geometry of the target region for which an infusion of the medical substance is intended, and a position and a geometry of an off-target region for which application of the medical substance is intended to be avoided;

acquiring, based on the acquired target region geometry data, target coverage data comprising target coverage information describing a planned coverage of the target and off-target regions by the medical substance, wherein the target coverage information comprises information describing a minimum dose of the medical substance to be infused into the target region and information describing a maximum dose of the medical substance to be applied to the off-target region;

acquiring, based on selecting a predetermined spatial distribution of the medical substance in the target region based on the target coverage data, relationship data comprising relationship information which describes a relationship between at least one physical parameter of the associated infusion setup and the selected predetermined spatial distribution of the medical substance, wherein the at least one physical parameter describes at least one of a geometric property of the infusion device, a surface property of the infusion device, a fluid dynamic property of the medical substance, and/or time; and determining infusion setup data comprising infusion setup information which describes a planned infusion setup, based on the relationship data and the target coverage data.

2. The method according to claim 1, wherein the geometric property of the infusion device comprises at least one of a tip length property, a diameter property and/or a number of outlets or position of a catheter used for the infusion of the medical substance.

3. The method according to claim 1, wherein the surface property of the infusion device comprises at least one of:
   a surface roughness of an inner and/or an outer surface of a catheter, and/or
   a topology of a catheter used for the infusion of the medical substance.

4. The method according to claim 1, wherein the fluid dynamic property of the infusion device comprises at least one of a pressure property, a flow rate property, a flow velocity property, a fluid resistance property, a viscosity property and/or a density property of the medical substance during the infusion.

5. The method according to claim 1, wherein the selected predetermined spatial distribution of the medical substance has a shape of a convex rotational solid and/or has a geometry which can be described by at least one geometric parameter.

6. The method according to claim 1, wherein the predetermined spatial distribution is selected based on the target region geometry data.

7. The method according to claim 1, wherein the at least one physical parameter of the associated setup is determined based on adapting the predetermined spatial distribution of the medical substance to fit the planned coverage of the target and off-target regions and, when the predetermined spatial distribution of the medical substance has a shape of rotational solid, the at least one physical parameter of the associated setup is determined based on adapting a parameter describing the geometry of the spatial distribution in order to adapt the predetermined spatial distribution of the medical substance to fit the planned coverage of the target and off-target regions.

8. The method according to claim 1, wherein the predetermined spatial distribution and the planned coverage of the target and off-target regions describe at least one of a geometry of the medical substance in the target region and/or a concentration distribution of the medical substance in the target region.

9. The method according to claim 1, further comprising determining the relationship data based on information about at least one geometric property of the infusion device and at least one fluid dynamic property of the medical substance.

10. The method according to claim 1, further comprising determining a medical treatment plan based on the infusion setup data.

11. The method according to claim 1, wherein all of the target region geometry data is acquired on the non-patient-specific basis from the associated atlas storing the predetermined standard anatomical data.

12. A computer program embodied on a non-transitory computer readable medium which, when running on a computer or when loaded onto a computer, causes the computer to perform a data processing method for planning an infusion of a medical substance into a target region of an anatomical body part, wherein the medical substance is to be infused using an associated infusion setup comprising the medical substance and an infusion device for performing the infusion, the method comprising:

- acquiring, on a non-patient-specific basis from an associated atlas storing predetermined standard anatomical data, target region geometry data, the target region geometry data comprising target region geometry information describing a position and a geometry of the target region for which an infusion of the medical substance is intended, and a position and a geometry of an off-target region for which application of the medical substance is intended to be avoided;
- acquiring, based on the acquired target region geometry data, target coverage data comprising target coverage information describing a planned coverage of the target and off-target regions by the medical substance, wherein the target coverage information comprises information describing a minimum dose of the medical substance to be infused into the target region and information describing a maximum dose of the medical substance to be applied to the off-target region;
- acquiring, based on selecting a predetermined spatial distribution of the medical substance in the target region based on the target coverage data, relationship data comprising relationship information which describes a relationship between at least one physical parameter of the associated infusion setup and the selected predetermined spatial distribution of the medical substance, wherein the at least one physical parameter describes at least one of a geometric property of the infusion device, a surface property of the infusion device, a fluid dynamic property of the medical substance, and/or time; and
- determining infusion setup data comprising infusion setup information which describes a planned infusion setup, based on the relationship data and the target coverage data.

13. The computer program according to claim 12, wherein all of the target region geometry data is acquired on the non-patient-specific basis from the associated atlas storing the predetermined standard anatomical data.

* * * * *

UNITED STATES PATENT AND TRADEMARK OFFICE
CERTIFICATE OF CORRECTION

PATENT NO. : 9,576,108 B2  
APPLICATION NO. : 14/371758  
DATED : February 21, 2017  
INVENTOR(S) : Kathryn H. Rosenbluth et al.

Page 1 of 1

It is certified that error appears in the above-identified patent and that said Letters Patent is hereby corrected as shown below:

On the Title Page

Please replace:
"(73) Assignee: Brainlab AG Munich (DE)"

With the following:
--(73) Assignee: Brainlab AG Munich (DE)
          The Regents of the University of California Oakland, California (US)--.

Signed and Sealed this
Sixth Day of June, 2017

Michelle K. Lee
*Director of the United States Patent and Trademark Office*